United States Patent
Nii et al.

(10) Patent No.: US 8,303,863 B2
(45) Date of Patent: Nov. 6, 2012

(54) INFRARED ABSORPTIVE COMPOUND, AND FINE PARTICLE CONTAINING THE COMPOUND

(75) Inventors: Kazumi Nii, Minami-ashigara (JP); Shunya Kato, Minami-ashigara (JP); Yoshihiro Jimbo, Fujinomiya (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 12/935,174

(22) PCT Filed: Mar. 27, 2009

(86) PCT No.: PCT/JP2009/056300
§ 371 (c)(1),
(2), (4) Date: Sep. 28, 2010

(87) PCT Pub. No.: WO2009/123056
PCT Pub. Date: Oct. 8, 2009

(65) Prior Publication Data
US 2011/0012075 A1 Jan. 20, 2011

(30) Foreign Application Priority Data
Mar. 30, 2008 (JP) .................................. 2008-088959

(51) Int. Cl.
| F21V 9/04 | (2006.01) |
| F21V 9/06 | (2006.01) |
| G02B 5/22 | (2006.01) |
| G02B 5/26 | (2006.01) |
| C04B 14/00 | (2006.01) |

(52) U.S. Cl. ........ 252/587; 106/311; 106/400; 106/401; 546/256; 548/181

(58) Field of Classification Search .................. 252/587, 252/301.16; 546/256, 276.7, 88; 548/181, 548/453; 104/401, 311, 400, 287.26; 106/311, 106/400, 401
See application file for complete search history.

(56) References Cited

U.S. PATENT DOCUMENTS

| 5,494,511 A | * | 2/1996 | Holbrook ...................... 524/141 |
| 2004/0151944 A1 | * | 8/2004 | Onikubo et al. .............. 428/690 |

FOREIGN PATENT DOCUMENTS

| EP | 1 452 574 A1 | 9/2004 |
| JP | 9-003448 A | 1/1997 |
| JP | 2003-027049 A | 1/2003 |
| WO | WO 03/048268 A1 | 6/2003 |
| WO | WO 2010/041769 A1 | 4/2010 |

OTHER PUBLICATIONS

Georg M. Fischer, Andreas P. Ehlers, Andreas Zumbusch, and Ewald Daltrozzo, Near-Infrared Dyes and Fluorophores Based on Diketopyrrolopyrroles, Angew. Chem. Int. Ed. 2007, 46, 3750-3753. 2007. Wiley-VCH Verlag GmbH & Co. KGaA, Weinheim.*
Organic chemistry pamphlet, Chapter 12, taken from Francis Carey and Robert Giuliano, Organic chemistry, McGraw-Hill Science/Engineering/Math; 8 edition (Jan. 8, 2010).*
International Search Report (PCT/ISA/210) issued on Apr. 28, 2009, by Japanese Patent Office as the International Searching Authority for International Application No. PCT/JP2009/056300.
Fischer et al., "Near-Infrared Dyes and Fluorophores Based on Diketopyrrolopyrroles", Angewandte Chemie, International Edition, 2007 (month unknown), pp. 3750-3753, vol. 46, No. 20.
Written Opinion of the International Search Authority (PCT/ISA/237) issued in corresponding International Application No. PCT/JP2009/056300 on Apr. 28, 2009 by Japanese Patent Office, and English Translation.
Extended Search Report issued by the European Patent Office issued in corresponding European Patent Application No. 09729036.5 dated Jul. 13, 2011.

* cited by examiner

*Primary Examiner* — Bijan Ahvazi
(74) *Attorney, Agent, or Firm* — Buchanan Ingersoll

(57) ABSTRACT

A fine particle which contains a compound represented by formula (1):

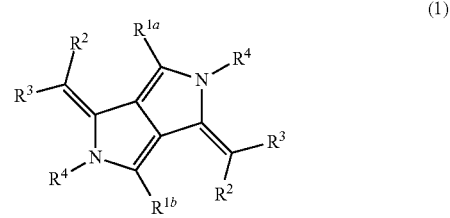

(1)

wherein $R^{1a}$ and $R^{1b}$ may be the same or different, and each independently represent an alkyl group, an aryl group, or a heteroaryl group; $R^2$ and $R^3$ each independently represent a hydrogen atom or a substituent, and at least one of $R^2$ and $R^3$ is an electron withdrawing group; $R^2$ may be bonded to $R^3$ to form a ring; $R^4$ represents a hydrogen atom, an alkyl group, an aryl group, a heteroaryl group, a substituted boron, or a metal atom; and $R^4$ may be covalently bonded or coordinately bonded to at least one among $R^{1a}$, $R^{1b}$ and $R^3$.

8 Claims, 2 Drawing Sheets

INFRARED ABSORPTIVE COMPOUND, AND FINE PARTICLE CONTAINING THE COMPOUND

TECHNICAL FIELD

The present invention relates to an infrared absorptive compound that shows absorption in a near-infrared range, but does not show absorption in a visible range, and a fine particle comprising the compound.

BACKGROUND ART

Near-infrared absorptive dyes are used for various purposes in wide fields. The dyes are used in, for example, infrared-cutting films for plasma display panels (PDP) or CCDs, optical filters in heat ray shield films, or photothermal conversion materials in write once optical disks (CD-R) or flash-meltable and fixable materials. Moreover, the dyes are used as information displaying materials for security inks or invisible bar code inks. For near-infrared absorptive dyes, it is very important that the dyes are excellent in invisibility, i.e., the property that the dyes are invisible, as well as the dyes show an intense absorption for rays in the near infrared range. Furthermore, for all dyes, a high durability (fastness) is required.

As dyes which hardly show an absorption in the wavelength range of 400 to 700 nm and are excellent in invisibility, cyanine methine dyes or J associations thereof can be mentioned. However, their long methine conjugated chain is flexible; thus, the dyes are easily isomerized so that the absorption wavelengths are changed, or the dyes are easily decomposed by heat or by reaction with oxygen or a nucleophilic agent. Accordingly, the dyes are low in fastness.

As near-infrared absorptive dyes having a rigid skeleton and a high fastness, there are vanadylnaphthalocyanine dyes suggested by Nippon Shokubai Co., Ltd., and quaterrylene dyes marketed by BASF AG. However, vanadylphthalocyanine dyes are insufficient in invisibility. The quaterrylene dyes have good invisibility in a state of molecular dispersion, for example, in a state of a solution of the dyes; however, when the concentration is made high, an absorption is generated for rays in the visible range by the association of the molecules so that the invisibility is lost. Thus, the way of use thereof is restricted.

As dyes that are excellent in invisibility and have an absorption for rays in the infrared range widely, there are diimmonium dyes marketed by Nippon Kayaku Co., Ltd. However, the dyes are easily reducible and are insufficient in fastness. Thus, the way for use thereof is restricted.

As described above, near-infrared absorptive dyes having both excellent invisibility and fastness have not been marketed up to date. Thus, it has been desired to develop near-infrared absorptive dyes having these performances compatibly with each other.

Further, pyrrolopyrrol dyes are known as a novel infrared absorptive dye (see, for example, Non-Patent Document 1). The Non-Patent Document 1 describes the results from a study on application of the pyrrolopyrrol dye to an infrared fluorescent dye. More specifically, the Non-Patent Document 1 describes that high-fluorescence quantum yield can be achieved by complexation of the pyrrolopyrrol dye with boron and by enhancing rigidity of the molecule. As an application for the fluorescent dye characteristic to this skeleton group, application to organic electroluminescent devices is known (see, for example, Patent Documents 1 to 3).

Generally, in order to emit high fluorescence, a fluorescent dye is used in such a dilute state that concentration quenching is not caused, and further the fluorescent dye is co-deposited with a host material and used in a molecular dispersion state. Further, it is known that such fluorescent dye generally shows low resistance to light.

[Patent Document 1] Japanese Patent No. 3704748
[Patent Document 2] JP-A-2003-027049 ("JP-A" means unexamined published Japanese patent application)
[Patent Document 3] WO2003/048268
[Non-Patent Document 1] Angewante Chemie International Edition of English, Vol. 46, pp. 3750 to 3753, 2007

SUMMARY OF INVENTION

The present invention provides a near-infrared absorptive dye which shows absorption in a near-infrared range, but does not show absorption in the range of 400 to 700 nm and which has excellent invisibility and high fastness. The present invention also provides a dye fine particle comprising the near-infrared absorptive dye. Further, the present invention provides a composition and a filter each using the dye or the dye fine particle. In order to achieve the above-mentioned subjects by pyrrolopyrrol dyes, improvement in both fastness (particularly light fastness) and invisibility is a subject to be addressed.

According to the present invention, there is provided the following means:

<1> A fine particle which comprises a compound represented by formula (1):

[Chemical formula 1]

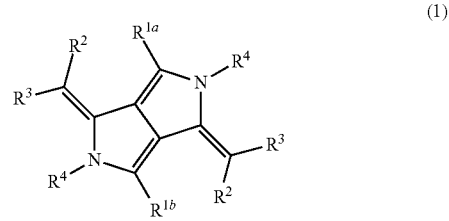

wherein $R^{1a}$ and $R^{1b}$ may be the same or different, and each independently represent an alkyl group, an aryl group, or a heteroaryl group; $R^2$ and $R^3$ each independently represent a hydrogen atom or a substituent, and at least one of $R^2$ and $R^3$ is an electron withdrawing group; $R^2$ may be bonded to $R^3$ to form a ring; $R^4$ represents a hydrogen atom, an alkyl group, an aryl group, a heteroaryl group, a substituted boron, or a metal atom; and $R^4$ may be covalently bonded or coordinately bonded to at least one among $R^{1a}$, $R^{1b}$ and $R^3$.

<2> The fine particle according to the above item <1>, wherein $R^3$ in formula (1) is a heterocyclic group.

<3> The fine particle according to the above item <1> or <2>, wherein the particle is an infrared absorptive particle which absorbs infrared rays in a wavelength range of 700 nm or more and 1000 nm or less.

<4> A composition which comprises the fine particle according to any one of the above items <1> to <3>.

<5> A coated material which comprises the fine particle according to any one of the above items <1> to <3>.

<6> An infrared absorptive compound represented by formula (2):

[Chemical formula 2]

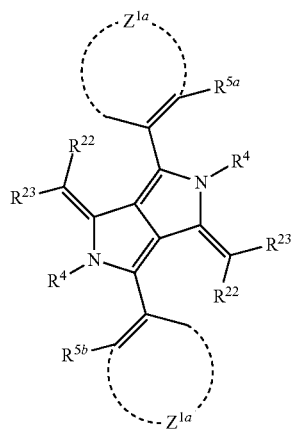

(2)

wherein, $Z^{1a}$ and $Z^{1b}$ each independently represent an atomic group that forms an aryl ring or a heteroaryl ring; $R^{5a}$ and $R^{5b}$ each independently represent an aryl group having 6 to 20 carbon atoms, a heteroaryl group having 4 to 20 carbon atoms, an alkyl group having 1 to 20 carbon atoms, an alkoxy group having 1 to 20 carbon atoms, an alkoxycarbonyl group having 1 to 20 carbon atoms, a carboxyl group, a carbamoyl group having 1 to 20 carbon atoms, a halogen atom, or a cyano group; $R^{5a}$ or $R^{5b}$ may be bonded to $Z^{1a}$ or $Z^{1b}$ to form a condensed ring; $R^{22}$ and $R^{23}$ each independently represent a cyano group, an acyl group having 1 to 6 carbon atoms, an alkoxycarbonyl group having 1 to 6 carbon atoms, an alkylsulfinyl or arylsufinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus; $R^4$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms; $R^4$ may be covalently bonded or coordinately bonded to $R^{23}$; the compound may further be substituted.

<7> An infrared absorptive compound represented by formula (3):

[Chemical formula 3]

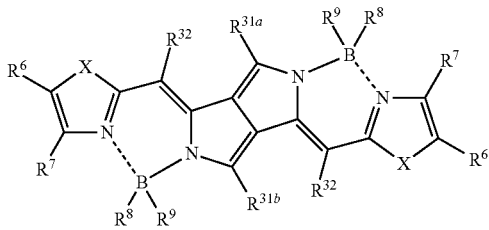

(3)

wherein, $R^{31a}$ and $R^{31b}$ each independently represent an alkyl group having 1 to 20 carbon atoms, an aryl group having 6 to 20 carbon atoms, or a heteroaryl group having 3 to 20 carbon atoms; $R^{32}$ represents a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms; $R^6$ and $R^7$ each independently represent a hydrogen atom, an alkyl group having 1 to 10 carbon atoms, an aryl group having 6 to 10 carbon atoms, or a heteroaryl group having 4 to 10 carbon atoms; $R^6$ may be bonded to $R^7$ to form a ring, and the formed ring is an alicyclic ring having 5 to 10 carbon atoms, an aryl ring having 6 to 10 carbon atoms, or a heteroaryl ring having 3 to 10 carbon atoms; $R^8$ and $R^9$ each independently represent an alkyl group having 1 to 10 carbon atoms, an alkoxy group having 1 to 10 carbon atoms, an aryl group having 6 to 20 carbon atoms, or a heteroaryl group having 3 to 10 carbon atoms; X represents an oxygen atom, a sulfur atom, —NR—, or —CRR'—; R and R' each independently represent a hydrogen atom, an alkyl group having 1 to 10 carbon atoms, or an aryl group having 6 to 10 carbon atoms.

<8> An infrared absorptive compound represented by formula (4):

[Chemical formula 4]

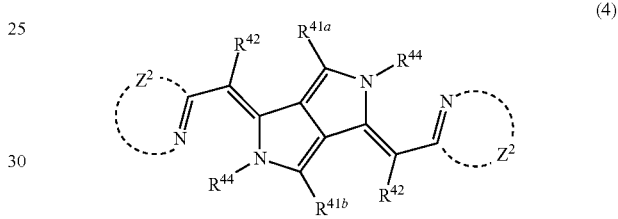

(4)

wherein, $R^{41a}$ and $R^{41b}$ represent groups different from each other and each represent an alkyl group having 1 to 20 carbon atoms, an aryl group having 6 to 20 carbon atoms, or a heteroaryl group having 3 to 20 carbon atoms; $R^{42}$ represent a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms; $Z^2$ represents an atomic group which is combined with —C=N— to form a 5- or 6-membered nitrogen-containing hetero ring, and the nitrogen-containing hetero ring represents a pyrazole ring, a thiazole ring, an oxazole ring, an imidazole ring, an oxadiazole ring, a thiadiazole ring, a triazole ring, a pyridine ring, a pyridazine ring, a pyrimidine ring, or a pyrazine ring; a benzo-condensed ring or a naphtho-condensed ring thereof; or a composite made from these condensed rings; $R^{44}$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms; $R^{44}$ may be covalently bonded or coordinately bonded to the nitrogen-containing hetero ring which $Z^2$ forms; the compound may further be be substituted.

The fine particle of the present invention which comprises the compound represented by the above-described formula (1) has properties that satisfy all of excellent infrared absorption characteristics, invisibility and fastness. Especially, when $R^3$ in formula (1) is a hetero ring, the fine particle shows excellent properties. Further, the fine particle can absorb selectively infrared rays of from 700 nm to 1000 nm.

Further, the composition and the coated material (ink and filter), in each of which the fine particle of the present invention is contained, each have excellent infrared absorbability, and each show both excellent fastness and excellent invisibility in combination.

The infrared absorptive compound resented by the above-described formula (2) of the present invention is a novel compound and has especially excellent invisibility. Further, the infrared absorptive compound resented by the above-described formula (3) of the present invention is also a novel compound and has both excellent fastness and excellent invisibility in combination. Further, the infrared absorptive compound resented by the above-described formula (4) of the present invention is also a novel compound and shows high fastness, high invisibility, excellent dispersibility and high solubility with respect to an organic solvent.

Figure 1:
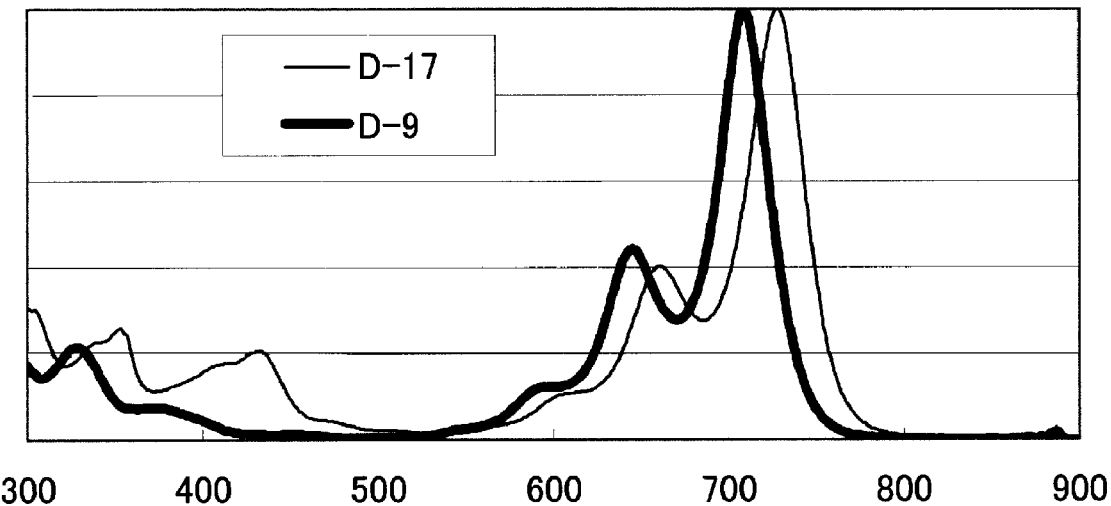
FIG. 1 is a graph showing solution absorption spectra in chloroform of exemplified compounds (D-17) and (D-9).

Other and further features and advantages of the invention will appear more fully from the following description, appropriately referring to the accompanying drawings.

MODE FOR CARRYING OUT INVENTION

Hereinafter, the present invention will be described in detail.

The fine particle of the present invention comprises a compound represented by the following formula (1). The fine particle of the present invention satisfies all of excellent infrared absorbability, invisibility and fastness.

[Chemical formula 5]

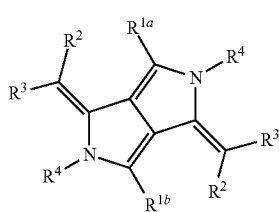

(1)

In formula (1), $R^{1a}$ and $R^{1b}$ may be the same as or different from each other, and each independently represent an alkyl group, an aryl group, or a heteroaryl group. $R^2$ and $R^3$ each independently represent a hydrogen atom or a substituent, and at least one of $R^2$ and $R^3$ is an electron withdrawing group. $R^2$ may be bonded to $R^3$ to form a ring. $R^4$ represents a hydrogen atom, an alkyl group, an aryl group, a heteroaryl group, a substituted boron, or a metal atom. $R^4$ may be covalently bonded or coordinately bonded to $R^{1a}$, $R^{1b}$ and/or $R^3$.

In formula (1), the alkyl group represented by each of $R^{1a}$ and $R^{1b}$ is an alkyl group having preferably 1 to 30 carbon atoms, more preferably 1 to 20 carbon atoms, and in particular preferably 1 to 10 carbon atoms (in any description for the present invention, the expression "A to B" wherein A and B each represent a number means numbers of "A or more and B or less"). Examples thereof include methyl, ethyl, iso-propyl, tert-butyl, n-octyl, n-decyl, n-hexadecyl, cyclopropyl, cyclopentyl, and cyclohexyl.

The aryl group represented by each of $R^{1a}$ and $R^{1b}$ is an aryl group having preferably 6 to 30 carbon atoms, more preferably 6 to 20 carbon atoms, and in particular preferably 6 to 12 carbon atoms. Examples thereof include phenyl, o-methylphenyl, p-methylphenyl, biphenyl, naphthyl, anthranyl, and phenanthryl.

The heteroaryl group represented by each of $R^{1a}$ and $R^{1b}$ is a heteroaryl group having preferably 1 to 30 carbon atoms, and more preferably 1 to 12 carbon atoms; and having, as hetero atom(s), a nitrogen atom, an oxygen atom and/or a sulfur atom. Examples thereof include imidazolyl, pyridyl, quinolyl, furyl, thienyl, benzoxazolyl, benzimidazolyl, benzothiazolyl, naphthothiazolyl, benzoxazolyl, m-carbazolyl, and azepinyl.

In formula (1), $R^{1a}$ and $R^{1b}$ may be the same as or different from each other.

$R^2$ and $R^3$ each independently represent a hydrogen atom or a substituent provided that at least one of $R^2$ and $R^3$ is an electron withdrawing group. $R^2$ may be bonded to $R^3$ to form a ring. Examples of the substituent include an alkyl group (having preferably 1 to 30 carbon atoms, more preferably 1 to 20 carbon atoms, and particularly preferably 1 to 10 carbon atoms, such as methyl, ethyl, iso-propyl, tert-butyl, n-octyl, n-decyl, n-hexadecyl, cyclopropyl, cyclopentyl, cyclohexyl), an alkenyl group (having preferably 2 to 30 carbon atoms, more preferably 2 to 20 carbon atoms, and particularly preferably 2 to 10 carbon atoms, such as vinyl, allyl, 2-butenyl, and 3-pentenyl), an alkynyl group (having preferably 2 to 30 carbon atoms, more preferably 2 to 20 carbon atoms, and particularly preferably 2 to 10 carbon atoms, such as propargyl and 3-pentynyl), an aryl group (having preferably 6 to 30 carbon atoms, more preferably 6 to 20 carbon atoms, and particularly preferably 6 to 12 carbon atoms, such as phenyl, p-methylphenyl, biphenyl, naphthyl, anthranyl, and phenanthryl), an amino group (having preferably 0 to 30 carbon atoms, more preferably 0 to 20 carbon atoms, and particularly preferably 0 to 10 carbon atoms, including alkylamino, arylamino, and heterocyclic amino group, such as amino, methylamino, dimethylamino, diethylamino, dibenzylamino, diphenylamino, and ditolylamino), an alkoxy group (having preferably 1 to 30 carbon atoms, more preferably 1 to 20 carbon atoms, and particularly preferably 1 to 10 carbon atoms, such as methoxy, ethoxy, butoxy, and 2-ethylhexyloxy), an aryloxy group (having preferably 6 to 30 carbon atoms, more preferably 6 to 20 carbon atoms, and particularly preferably 6 to 12 carbon atoms, such as phenyloxy, 1-naphthyloxy, and 2-naphthyloxy), an aromatic heterocyclic oxy group (having preferably 1 to 30 carbon atoms, more preferably 1 to 20 carbon atoms, and particularly preferably 1 to 12 carbon atoms, such as pyridyloxy, pyrazyloxy, pyrimidyloxy, quinolyloxy), an acyl group (having preferably 1 to 30 carbon atoms, more preferably 1 to 20 carbon atoms, and particularly preferably 1 to 12 carbon atoms, such as acetyl, benzoyl, formyl, and pivaloyl), an alkoxycarbonyl group (having preferably 2 to 30 carbon atoms, more preferably 2 to 20 carbon atoms, and particularly preferably 2 to 12 carbon atoms, such as methoxycarbonyl and ethoxycarbonyl), an aryloxycarbonyl group (having preferably 7 to 30 carbon atoms, more preferably 7 to 20 carbon atoms, and particularly preferably 7 to 12 carbon atoms, such as phenyloxycarbonyl), an acyloxy group (having preferably 2 to 30 carbon atoms, more preferably 2 to 20 carbon atoms, and particularly preferably 2 to 10 carbon atoms, such as acetoxy and benzoyloxy), an acylamino group (having preferably 2 to 30 carbon atoms, more preferably 2 to 20 carbon atoms, and particularly preferably 2 to 10 carbon atoms, such as acetylamino and benzoylamino), an alkoxycarbonylamino group (having preferably 2 to 30 carbon atoms, more preferably 2 to 20 carbon atoms, and particularly preferably 2 to 12 carbon atoms, such as methoxycarbonylamino), an aryloxycarbonylamino group (having preferably 7 to 30 carbon atoms, more preferably 7 to 20 carbon atoms, and particularly preferably 7 to 12 carbon atoms, such as phenyloxycarbonylamino), a sulfonylamino group (having preferably 1 to 30 carbon atoms, more preferably 1 to 20 carbon atoms, and particularly preferably 1 to 12 carbon atoms, such as methanesulfonylamino and benzenesulfonylamino), a sulfamoyl group (having preferably 0 to 30 carbon atoms, more preferably 0 to 20 carbon atoms, and particularly preferably 0 to 12 carbon atoms, such as sulfamoyl, methylsulfamoyl, dimethylsulfamoyl, and phenylsulfamoyl), a carbamoyl group (having preferably 1 to 30 carbon atoms, more preferably 1 to 20 carbon atoms, and particularly preferably 1 to 12 carbon atoms, such as carbamoyl, methylcarbamoyl, diethylcarbamoyl, and phenylcarbamoyl), an alkylthio group (having preferably 1 to 30 carbon atoms, more preferably 1 to 20 carbon atoms, and particularly preferably 1 to 12 carbon atoms, such as methylthio and ethylthio), an arylthio group (having preferably 6 to 30 carbon atoms, more preferably 6 to 20 carbon atoms, and particularly preferably 6 to 12 carbon atoms, such as phenylthio),
an aromatic heterocyclic thio group (having preferably 1 to 30 carbon atoms, more preferably 1 to 20 carbon atoms, and particularly preferably 1 to 12 carbon atoms, such as pyridylthio, 2-benzimizolylthio, 2-benzoxazolylthio, 2-benzothiazolylthio), a sulfonyl group (having preferably 1 to 30 carbon atoms, more preferably 1 to 20 carbon atoms, and particularly preferably 1 to 12 carbon atoms, such as mesyl and tosyl), a sulfinyl group (having preferably 1 to 30 carbon atoms, more preferably 1 to 20 carbon atoms, and particularly preferably 1 to 12 carbon atoms, such as methanesulfinyl and benzenesulfinyl), a ureido group (having preferably 1 to 30 carbon atoms, more preferably 1 to 20 carbon atoms, and particularly preferably 1 to 12 carbon atoms, such as ureido, methylureido, and phenylureido), a phosphoric acid amide group (having preferably 1 to 30 carbon atoms, more preferably 1 to 20 carbon atoms, and particularly preferably 1 to 12 carbon atoms, such as diethylphosphoric acid amide and phenylphosphoric acid amide), a hydroxyl group, a mercapto group, a halogen atom (such as a fluorine atom, a chlorine atom, a bromine atom, and an iodine atom), a cyano group, a sulfo group, a carboxyl group, a nitro group, a hydroxamic acid group, a sulfino group, a hydrazino group, an imino group, a heterocyclic group (having preferably 1 to 30 carbon atoms, and more preferably 1 to 12 carbon atoms where examples of the hetero atom are a nitrogen atom, an oxygen atom and a sulfur atom and, to be more specific, such as imidazolyl, pyridyl, quinolyl, furyl, thienyl, piperidyl, morpholino, benzoxazolyl, benzimidazolyl, benzothiazolyl, carbazolyl, and azepinyl group), and a silyl group (having preferably 3 to 40 carbon atoms, more preferably 3 to 30 carbon atoms, and particularly preferably 3 to 24 carbon atoms, such as trimethylsilyl and triphenylsilyl). These substituents may be further substituted.

The electron withdrawing group represented by $R^2$ or $R^3$ is preferably a electron withdrawing group having a Hammett $\sigma_p$ value (sigma para value) of 0.2 or more. Examples thereof include a cyano group, an acyl group, an alkyloxycarbonyl group, an aryloxycarbonyl group, a sulfamoyl group, a sulfinyl group, and a heterocyclic group. These electron withdrawing groups may be further substituted.

The expression "Hammett substituent constant $\sigma$ value" used herein will be described. Hammett's rule is a rule of thumb advocated by L. P. Hammett in 1935 for quantitatively considering the effect of substituents on the reaction or equilibrium of benzene derivatives, and the appropriateness thereof is now widely recognized. The substituent constant determined in the Hammett's rule involves $\sigma_p$ value and $\sigma_m$ value. These values can be found in a multiplicity of general publications, and are detailed in, for example, "Lange's Handbook of Chemistry" 12th edition by J. A. Dean, 1979 (McGraw-Hill), "Kagaku no Ryoiki" special issue, No. 122, pp. 96 to 103, 1979 (Nankodo) and Chem. Rev., vol. 91, pp. 165 to 195, 1991. In the present invention, the substituent having a Hammett substituent constant $\sigma_p$ value of 0.2 or more means that this substituent is an electron withdrawing group. The $\sigma_p$ value is preferably 0.25 or more, more preferably 0.3 or more, and in particular preferably 0.35 or more.

Examples thereof include a cyano group (0.66), a carboxyl group (—COOH: 0.45), an alkoxycarbonyl group (e.g. —COOMe: 0.45), an aryloxycarbonyl group (e.g. —COOPh: 0.44), a carbamoyl group (—CONH$_2$: 0.36), an alkylcarbonyl group (e.g. —COMe: 0.50), an arylcarbonyl group (e.g. —COPh: 0.43), an alkylsulfonyl group (e.g. —SO$_2$Me: 0.72), and an arylsulfonyl group (e.g. —SO$_2$Ph: 0.68). In the present description, Me represents a methyl group and Ph represents a phenyl group. The values in parentheses are the $\sigma_p$ values of typical substituents, as extracted from Chem. Rev., 1991, vol. 91, p. 165 to 195.

When $R^2$ and $R^3$ in formula (1) are combined to form a ring, the ring formed is preferably a 5- to 7-membered ring (preferably 5- or 6-membered ring) which is usually used as an acidic nucleus in a merocyanine dye, and specific examples thereof include the followings:

(a) a 1,3-dicarbonyl nucleus, such as 1,3-indanedione nucleus, 1,3-cyclohexanedione, 5,5-dimethyl-1,3-cyclohexanedione, and 1,3-dioxane-4,6-dione, (b) a pyrazolinone nucleus, such as 1-phenyl-2-pyrazolin-5-one, 3-methyl-1-phenyl-2-pyrazolin-5-one, and 1-(2-benzothiazoyl)-3-methyl-2-pyrazolin-5-one, (c) an isoxazolinone nucleus, such as 3-phenyl-2-isoxazolin-5-one, and 3-methyl-2-isoxazolin-5-one, (d) an oxyindole nucleus, such as 1-alkyl-2,3-dihydro-2-oxyindole, (e) a 2,4,6-triketohexahydropyrimidine nucleus, such as barbituric acid, 2-thiobarbituric acid and a derivative thereof; examples of the derivative include a 1-alkyl form such as 1-methyl and 1-ethyl, a 1,3-dialkyl form such as 1,3-dimethyl, 1,3-diethyl and 1,3-dibutyl, a 1,3-diaryl form such as 1,3-diphenyl, 1,3-di(p-chlorophenyl) and 1,3-di(p-ethoxycarbonylphenyl), a 1-alkyl-1-aryl form such as 1-ethyl-3-phenyl, and a 1,3-diheterocyclic substitution form such as 1,3-di(2-pyridyl), (f) a 2-thio-2,4-thiazolidinedione nucleus, such as rhodanine and a derivative thereof; examples of the derivative include a 3-alkylrhodanine such as 3-methylrhodanine, 3-ethylrhodanine and 3-allylrhodanine, a 3-arylrhodanine such as 3-phenylrhodanine, and a 3-heterocyclic ring-substituted rhodanine such as 3-(2-pyridyl)rhodanine, (g) a 2-thio-2,4-oxazolidinedione (2-thio-2,4-(3H,5H)-oxazoledione) nucleus, such as 3-ethyl-2-thio-2,4-oxazolidinedione,
(h) a thianaphthenone nucleus, such as 3(2H)-thianaphthenone-1,1-dioxide,
(i) a 2-thio-2,5-thiazolidinedione nucleus, such as 3-ethyl-2-thio-2,5-thiazolidinedione,
(j) a 2,4-thiazolidinedione nucleus, such as 2,4-thiazolidinedione, 3-ethyl-2,4-thiazolidinedione and 3-phenyl-2,4-thiazolidinedione,
(k) a thiazolin-4-one nucleus, such as 4-thiazolinone and 2-ethyl-4-thiazolinone,
(l) a 4-thiazolidinone nucleus, such as 2-ethylmercapto-5-thiazolin-4-one and 2-alkylphenylamino-5-thiazolin-4-one,
(m) a 2,4-imidazolidinedione (hydantoin) nucleus, such as 2,4-imidazolidinedione and 3-ethyl-2,4-imidazolidinedione,
(n) a 2-thio-2,4-imidazolidinedione (2-thiohydantoin) nucleus, such as 2-thio-2,4-imidazolidinedione and 3-ethyl-2-thio-2,4-imidazolidinedione,
(o) an imidazolin-5-one nucleus, such as 2-propylmercapto-2-imidazolin-5-one,
(p) a 3,5-pyrazolidinedione nucleus, such as 1,2-diphenyl-3,5-pyrazolidinedione and 1,2-dimethyl-3,5-pyrazolidinedione,
(q) a benzothiophen-3-one nucleus, such as benzothiophen-3-one, oxobenzothiophen-3-one and dioxobenzothiophen-3-one, and
(r) an indanone nucleus, such as 1-indanone, 3-phenyl-1-indanone, 3-methyl-1-indanone, 3,3-diphenyl-1-indanone and 3,3-dimethyl-1-indanone.

When $R^2$ is bonded to $R^3$ to form a ring, the σp value of $R^2$ and $R^3$ cannot be specified. However, in the present invention, the σp values of $R^2$ and $R^3$ are defined with assuming that partial structures of the ring are substituted as $R^2$ and $R^3$. For example, when $R^2$ and $R^3$ form a 1,3-indandione ring, it is supposed that benzoyl groups are substituted as $R^2$ and $R^3$.

The ring formed by $R^2$ and $R^3$ is preferably a 1,3-dicarbonyl nucleus, a pyrazolinone nucleus, a 2,4,6-triketohexahydropyrimidine nucleus (including a thioketone form), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, a 3,5-pyrazolidinedione nucleus, a benzothiophen-3-one nucleus or an indanone nucleus; and more preferably a 1,3-dicarbonyl nucleus, a 2,4,6-triketohexahydropyrimidine nucleus (including a thioketone form), a 3,5-pyrazolidinedione nucleus, a benzothiophen-3-one nucleus or an indanone nucleus.

$R^3$ is in particular preferably a heterocyclic group (a hetero ring).

Two groups represented by $R^2$ in formula (1) may be the same as or different from each other, and two groups represented by $R^3$ may be the same as or different from each other.

The alkyl group, the aryl group and the heteroaryl group represented by $R^4$ have the same meanings of those described as $R^{1a}$ and $R^{1b}$, respectively. Preferred ranges thereof are also the same. The substituent in the substituted boron represented by $R^4$ has the same meaning as the substituent described about $R^2$ and $R^3$. Preferred examples thereof include an alkyl group, an aryl group, and a heteroaryl group. The metal atom represented by $R^4$ is preferably a transition metal, magnesium, aluminum, calcium, barium, zinc or tin, more preferably aluminum, zinc, tin, vanadium, iron, cobalt, nickel, copper, palladium, iridium or platinum, and in particular preferably aluminum, zinc, vanadium, iron, copper, palladium, iridium or platinum.

$R^4$ may be covalently bonded or coordinately bonded to $R^{1a}$, $R^{1b}$ and/or $R^3$.

In formula (1), two groups represented by $R^4$ may be the same as or different from each other.

The compound represented by formula (1) is preferably an infrared absorptive compound represented by any one of the following formulae (2), (3) and (4):

[Chemical formula 6]

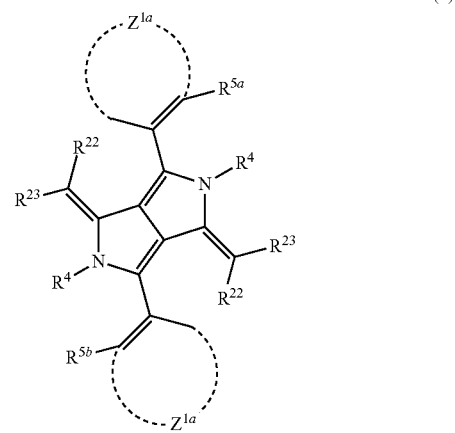

(2)

In formula (2), $Z^{1a}$ and $Z^{1b}$ each independently represent an atomic group that forms an aryl ring or a heteroaryl ring. $R^{5a}$ and $R^{5b}$ each independently represent an aryl group having 6 to 20 carbon atoms, a heteroaryl group having 4 to 20 carbon atoms, an alkyl group having 1 to 20 carbon atoms, an alkoxy group having 1 to 20 carbon atoms, an alkoxycarbonyl group having 1 to 20 carbon atoms, a carboxyl group, a carbamoyl group having 1 to 20 carbon atoms, a halogen atom, or a cyano group. $R^{5a}$ or $R^{5b}$ may be bonded to or $Z^{1a}$ or $Z^{1b}$ to form a condensed ring. $R^{22}$ and $R^{23}$ each independently represent a cyano group, an acyl group having 1 to 6 carbon atoms, an alkoxycarbonyl group having 1 to 6 carbon atoms, an alkylsulfinyl or arylsufinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus. $R^4$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms. $R^4$ may be covalently bonded or coordinately bonded to $R^{23}$. The above compound may further be substituted.

[Chemical formula 7]

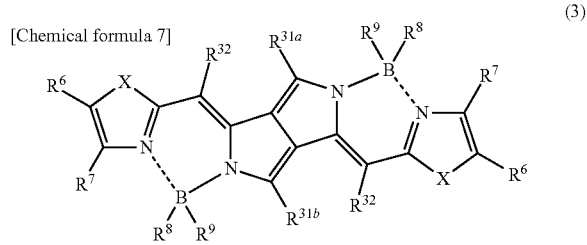

(3)

In formula (3), $R^{31a}$ and $R^{31b}$ each independently represent an alkyl group having 1 to 20 carbon atoms, an aryl group having 6 to 20 carbon atoms, or a heteroaryl group having 3 to 20 carbon atoms. $R^{32}$ represents a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms. $R^6$ and $R^7$ each independently represent a hydrogen atom, an alkyl group having 1 to 10 carbon atoms, an aryl group having 6 to 10 carbon atoms, or a heteroaryl group having 4 to 10 carbon atoms. $R^6$ may be bonded to $R^7$ to form a ring. The formed ring is an alicyclic ring having 5 to 10 carbon atoms, an aryl ring having 6 to 10 carbon atoms, or a heteroaryl ring having 3 to 10 carbon atoms. $R^8$ and $R^9$ each independently represent an alkyl group having 1 to 10 carbon atoms, an alkoxy group having 1 to 10 carbon atoms, an aryl group having 6 to 20 carbon atoms, or a heteroaryl group having 3 to 10 carbon atoms. X represents an oxygen atom, a sulfur atom, —NR—, or —CRR'—, wherein R and R' each independently represent a hydrogen atom, an alkyl group having 1 to 10 carbon atoms, or an aryl group having 6 to 10 carbon atoms.

[Chemical formula 8]

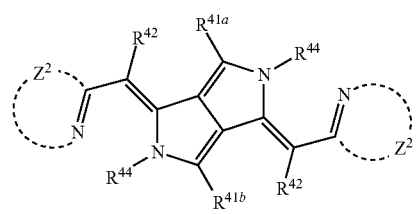

(4)

In formula (4), $R^{41a}$ and $R^{41b}$ represent groups different from each other and each represent an alkyl group having 1 to 20 carbon atoms, an aryl group having 6 to 20 carbon atoms, or a heteroaryl group having 3 to 20 carbon atoms. $R^{42}$ represent a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms. $Z^2$ represents an atomic group which is combined with —C=N— to form a 5- or 6-membered nitrogen-containing hetero ring. The nitrogen-containing hetero ring represents a pyrazole ring, a thiazole ring, an oxazole ring, an imidazole ring, an oxadiazole ring, a thiadiazole ring, a triazole ring, a pyridine ring, a pyridazine ring, a pyrimidine ring, or a pyrazine ring; a benzo-condensed ring or a naphtho-condensed ring thereof; or a composite made from these condensed rings. $R^{44}$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms. $R^{44}$ may be covalently bonded or coordinately bonded to the nitrogen-containing hetero ring which $Z^2$ forms. The above compound may further be substituted.

The compound represented by formula (2) will be described hereinafter.

In formula (2), $Z^{1a}$ and $Z^{1b}$ each independently represent an atomic group that forms an aryl ring or a heteroaryl ring. The formed aryl ring or heteroaryl ring has the same meaning as the aryl group or heteroaryl group described about the substituent as each of $R^2$ and $R^3$ in formula (1). A preferred range of the formed aryl ring or heteroaryl ring is also the same. $Z^{1a}$ and $Z^{1b}$ are preferably the same as each other.

$R^{5a}$ and $R^{5b}$ each independently represent an aryl group having 6 to 20 carbon atoms, a heteroaryl group having 4 to 20 carbon atoms, an alkyl group having 1 to 20 carbon atoms, an alkoxy group having 1 to 20 carbon atoms, an alkoxycarbonyl group having 1 to 20 carbon atoms, a carboxyl group, a carbamoyl group having 1 to 20 carbon atoms, a halogen atom, or a cyano group. Specific examples thereof are the same as described about $R^2$ and $R^3$ in formula (1). Preferred ranges thereof are also the same. $R^{5a}$ and $R^{5b}$ are preferably the same as each other.

$R^{5a}$ or $R^{5b}$ may be bonded to $Z^{1a}$ or $Z^{1b}$ to form a condensed ring. Examples of the condensed ring include a naphthyl ring and a quinoline ring.

By introducing the group represented by $R^{5a}$ or $R^{5b}$ into the aryl ring or heteroaryl ring that $Z^{1a}$ or $Z^{1b}$ forms, the invisibility can be largely improved.

$R^{22}$ and $R^{23}$ each independently represent a cyano group, an acyl group having 1 to 6 carbon atoms, an alkoxycarbonyl group having 1 to 6 carbon atoms, an alkylsufinyl or arylsufinyl group having 1 to 10 carbon atoms, or a nitrogen-containing heteroaryl group having 3 to 20 carbon atoms, or $R^{22}$ is bonded to $R^{23}$ to form a cyclic acidic nucleus. Specific examples thereof are the same as described about $R^2$ and $R^3$ in formula (1). Preferred ranges thereof are also the same. $R^4$ has the same meaning as $R^4$ in formula (1). A Preferred range thereof is also the same. $R^4$ may be covalently bonded or coordinately bonded to $R^{23}$.

The compound represented by formula (2) may further have a substituent. The substituent has the same meaning as the substituent as each of $R^2$ and $R^3$. A preferred range thereof is also the same.

In formula (2), a preferred combination of $Z^{1a}$, $Z^{1b}$ and the like is as follows: $Z^{1a}$ and $Z^{1b}$ each independently form a benzene ring or a pyridine ring; $R^{5a}$ and $R^{5b}$ are each independently an alkyl group, an alkoxy group, a halogen atom, or a cyano group; $R^{22}$ and $R^{23}$ are each independently a heterocyclic group, a cyano group, an acyl group, or an alkoxycarbonyl group, or $R^{22}$ is bonded to $R^{23}$ to form a cyclic acidic nucleus; and $R^4$ is a hydrogen atom, a substituted boron, a transition metal atom, magnesium, aluminum, calcium, barium, zinc, or tin. A particularly preferred combination thereof is as follows: $Z^{1a}$ and $Z^{1b}$ each form a benzene ring; $R^{5a}$ and $R^{5b}$ are each an alkyl group, a halogen atom, or a cyano group; $R^{22}$ and $R^{23}$ are each independently a combination of a nitrogen-containing heterocyclic group with a cyano group or alkoxycarbonyl group, or $R^{22}$ is bonded to $R^{23}$ to form a cyclic acidic nucleus; and $R^4$ is a hydrogen atom, a substituted boron, aluminum, zinc, vanadium, iron, copper, palladium, iridium or platinum.

The compound represented by formula (3) will be described hereinafter.

In formula (3), $R^{31a}$ and $R^{31b}$ each independently represent an alkyl group having 1 to 20 carbon atoms, an aryl group having 6 to 20 carbon atoms, or a heteroaryl group having 3 to 20 carbon atoms. Specific examples thereof are the same as described about $R^{1a}$ and $R^{1b}$ in formula (1). Preferred ranges thereof are also the same. $R^{31a}$ and $R^{31b}$ are preferably the same as each other.

$R^{32}$ is a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms. Specific examples thereof are the same as described about $R^2$ in formula (1). A preferred range thereof is also the same.

$R^6$ and $R^7$ are each independently a hydrogen atom, an alkyl group having 1 to 10 carbon atoms, an aryl group having 6 to 10 carbon atoms, or a heteroaryl group having 4 to 10 carbon atoms. Specific examples thereof are the same as described about the substituents as $R^2$ and $R^3$ in formula (1). Preferred ranges thereof are also the same. $R^6$ may be bonded to $R^7$ to form a ring. The formed ring is an alicyclic ring having 5 to 10 carbon atoms, an aryl ring having 6 to 10 carbon atoms, or a heteroaryl ring having 3 to 10 carbon atoms. Preferred examples thereof include a benzene ring, a naphthalene ring or a pyridine ring.

By introducing a 5-membered, nitrogen-containing hetero ring substituted by $R^6$ and $R^7$, and further modifying the compound to a boron complex, a near-infrared absorptive dye having a high fastness and a high invisibility, which are compatible with each other, can be realized.

$R^8$ and $R^9$ are each independently an alkyl group having 1 to 10 carbon atoms, an alkoxy group having 1 to 10 carbon atoms, an aryl group having 6 to 20 carbon atoms, or a heteroaryl group having 3 to 10 carbon atoms. Specific examples thereof are the same as described about the substituents as $R^2$ and $R^3$ in formula (1). Preferred ranges thereof are also the same.

X represents an oxygen atom, a sulfur atom, —NR—, or —CRR'—, wherein R and R' each independently represent a hydrogen atom, an alkyl group having 1 to 10 carbon atoms, or an aryl group having 6 to 10 carbon atoms, and are each preferably a hydrogen atom, an alkyl group having 1 to 6 carbon atoms, or a phenyl group.

In formula (3), a preferred combination of $R^{31a}$, $R^{31b}$ and the like is as follows: $R^{31a}$ and $R^{31b}$ are each independently an alkyl group having 1 to 10 carbon atoms, a benzene ring, or a pyridine ring; $R^{32}$ is a cyano group or an alkoxycarbonyl group; $R^6$ is bonded to $R^7$ to form a benzene ring, a pyridine ring, a pyrazine ring, or a pyrimidine ring; $R^8$ and $R^9$ are each independently an alkyl group having 1 to 6 carbon atoms, a phenyl group or a naphthyl group; and X is an oxygen atom, a sulfur atom, —NR—, or —CRR'—, wherein R and R' each independently represent a hydrogen atom, an alkyl group having 1 to 6 carbon atoms, or a phenyl group. A particularly preferred combination thereof is as follows: $R^{31a}$ and $R^{31b}$ are each an alkyl group having 1 to 10 carbon atoms, or a benzene ring; $R^{32}$ is a cyano group; $R^6$ is bonded to $R^7$ to form a benzene ring, or a pyridine ring; $R^8$ and $R^9$ are each independently an alkyl group having 1 to 6 carbon atoms, a phenyl group or a naphthyl group; and X is an oxygen atom or a sulfur atom.

The compound represented by formula (4) will be described hereinafter.

In formula (4), $R^{41a}$ and $R^{41b}$ each represent an alkyl group having 1 to 20 carbon atoms, an aryl group having 6 to 20 carbon atoms, or a heteroaryl group having 3 to 20 carbon atoms. Specific examples thereof are the same as described about $R^{1a}$ and $R^{1b}$ in formula (1). Preferred ranges thereof are also the same. However, $R^{41a}$ and $R^{41b}$ represent groups different from each other.

$R^{42}$ is a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms. Specific examples thereof are the same as described about $R^2$ in formula (1). A preferred range thereof is also the same.

$Z^2$ represents an atomic group which is combined with —C=N— to form a 5- or 6-membered nitrogen-containing hetero ring. The nitrogen-containing hetero ring represents a pyrazole ring, a thiazole ring, an oxazole ring, an imidazole ring, an oxadiazole ring, a thiadiazole ring, a triazole ring, a pyridine ring, a pyridazine ring, a pyrimidine ring, or a pyrazine ring; a benzo-condensed ring or a naphtho-condensed ring thereof; or a composite made from these condensed rings.

$R^{44}$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms. $R^{44}$ may be covalently bonded or coordinately bonded to the nitrogen-containing hetero ring which $Z^2$ forms.

$R^{41a}$ and $R^{41b}$, which are different from each other, are introduced, and the 5- or 6-membered nitrogen-containing hetero ring, which is made from $Z^2$ and —C=N—, is introduced, whereby a high fastness, a high invisibility, an excellent dispersibility and a high solubility in organic solvent can be obtained.

In formula (4), a preferred combination of $R^{41a}$, $R^{41b}$ and the like are as follows: $R^{41a}$ and $R^{41b}$ are each independently an alkyl group having 1 to 10 carbon atoms, a benzene ring, or a pyridine ring; $R^{42}$ is a cyano group, an alkylsulfinyl or arylsulfinyl group having 1 to 10 carbon atoms, or an alkoxycarbonyl group having 1 to 10 carbon atoms; $Z^2$ is combined with —C=N— to form a thiazole ring, an oxazole ring, an imidazole ring, a thiadiazole ring, a triazole ring, a pyridine ring, a pyrimidine ring or a pyrazine ring, or a benzo-condensed ring or a naphtho-condensed ring thereof; and $R^{44}$ is a hydrogen atom, a substituted boron, a transition metal atom, magnesium, aluminum, calcium, barium, zinc, or tin. A particularly preferred combination thereof is as follows: $R^{41a}$ and $R^{41b}$ are each independently an alkyl group having 1 to 10 carbon atoms, or a benzene ring; $R^{42}$ is a cyano group; $Z^2$ is combined with —C=N— to form a thiazole ring, an oxazole ring, an imidazole ring, a triazole ring, a pyridine ring or a pyrimidine ring, or a benzo-condensed ring or a naphtho-condensed ring thereof; and $R^{44}$ is a hydrogen atom, a substituted boron (its substituent is an alkyl group having 1 to 10 carbon atoms, a benzene ring, a pyridine ring, or a thiophene ring), aluminum, zinc, vanadium, iron, copper, palladium, iridium, or platinum.

Hereinafter, illustrated are specific examples of the compound (dye compound) represented by any one of formulae (1) to (4). In the present invention, the compound is not limited to the specific examples.

[Chemical formula 9]
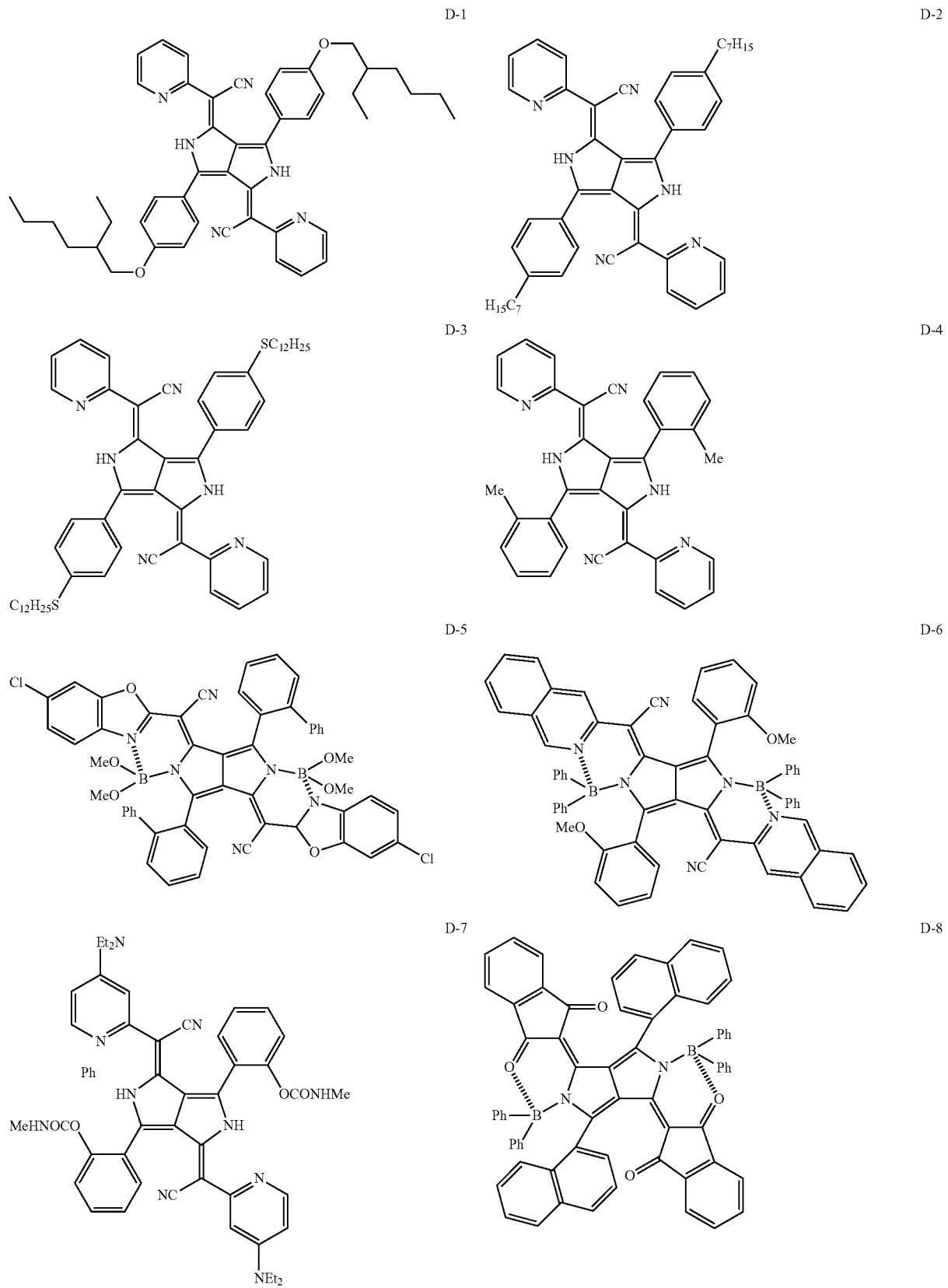

[Chemical formula 10]
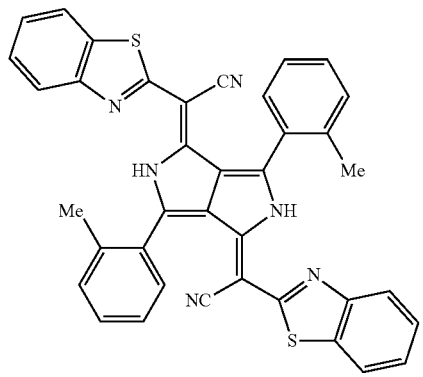
D-9
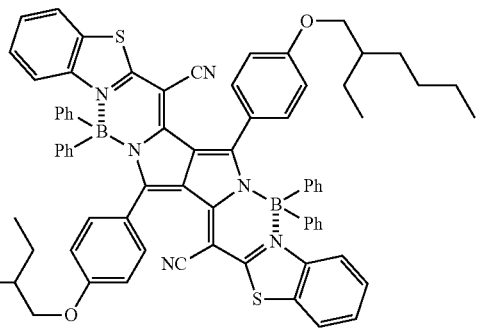
D-10
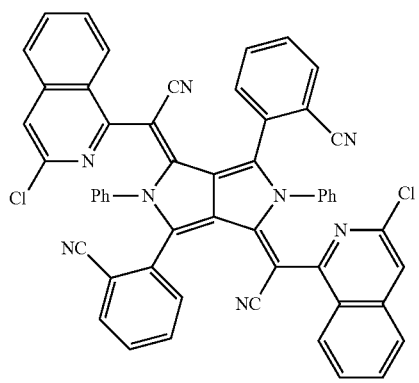
D-11
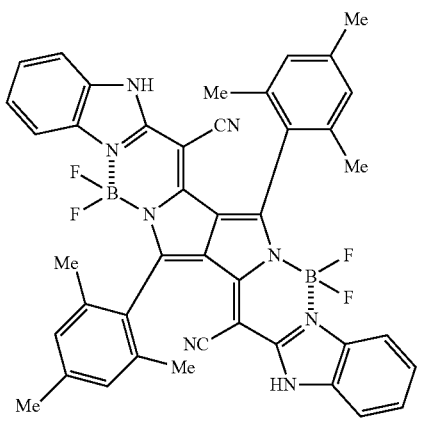
D-12
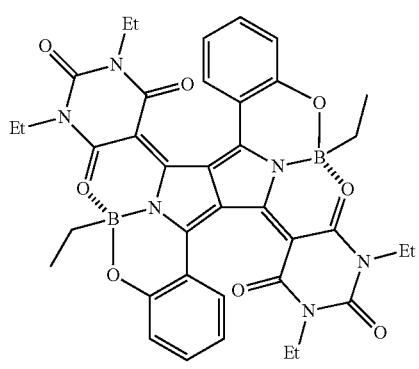
D-13
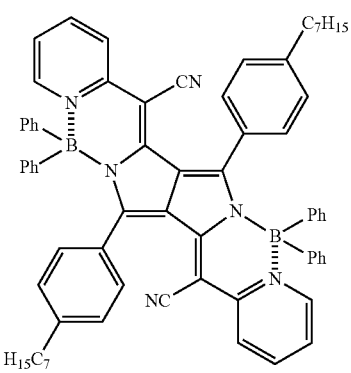
D-14

-continued
D-15
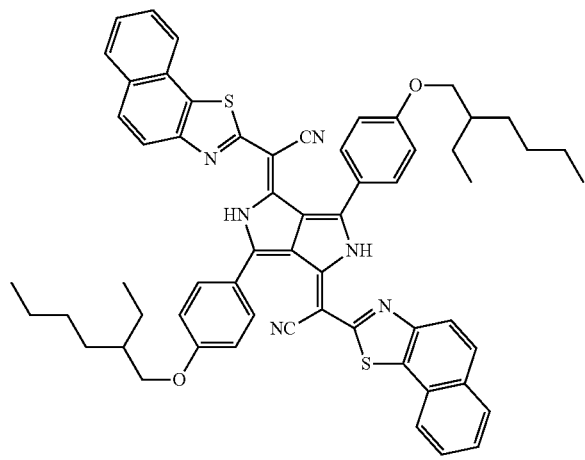
D-16
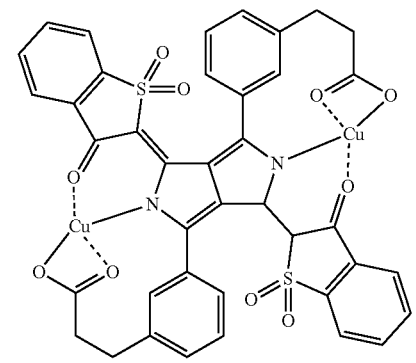
[Chemical formula 11]
D-17
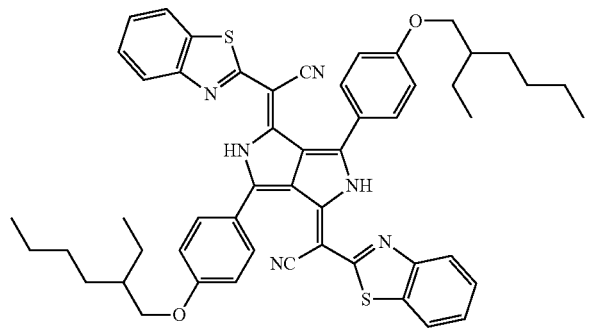
D-18
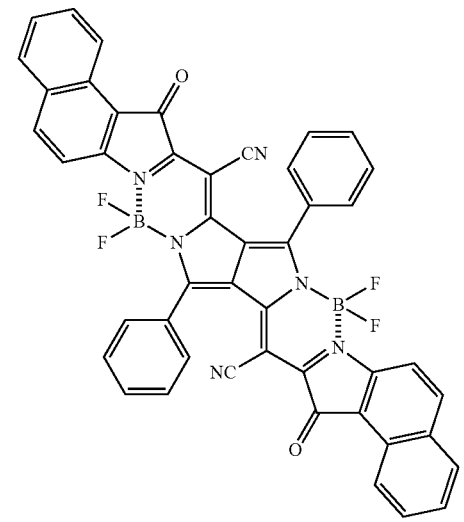
D-19
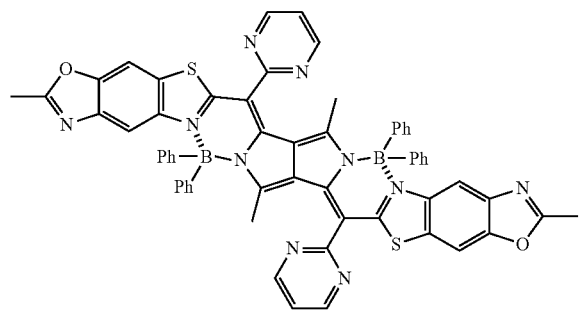
D-20
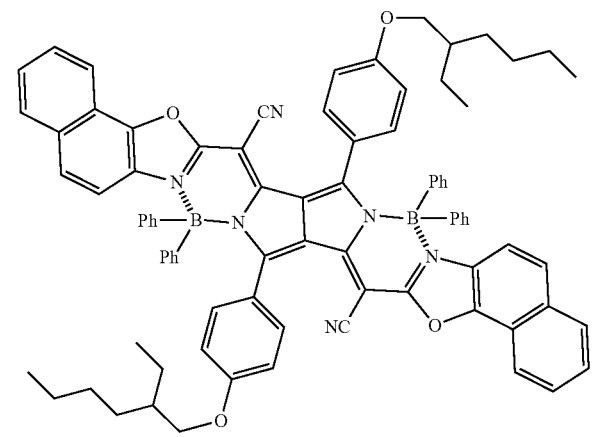

-continued
D-21
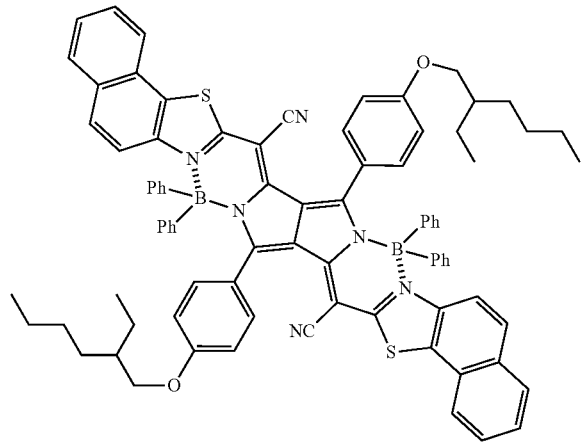
D-22
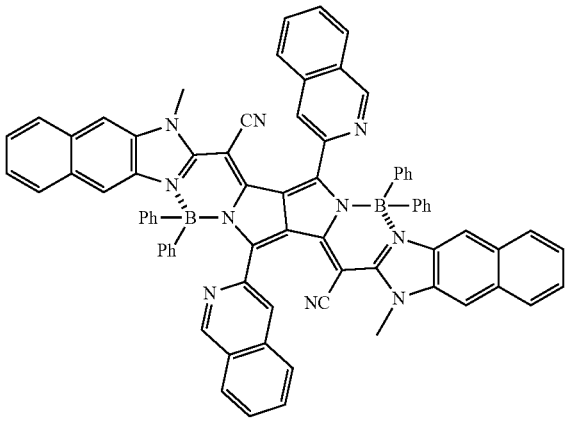
D-23
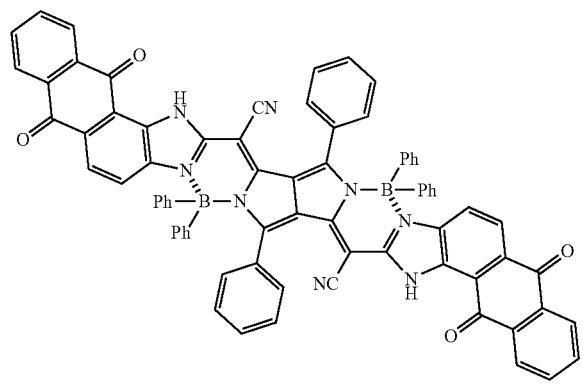
D-24
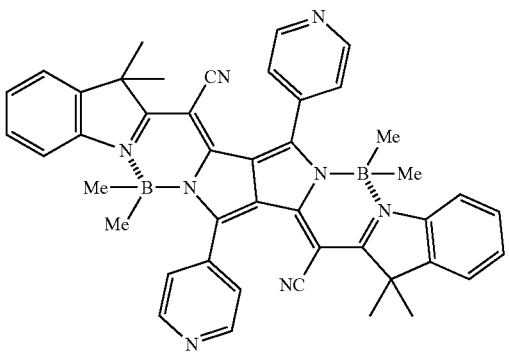
[Chemical formula 12]
D-25
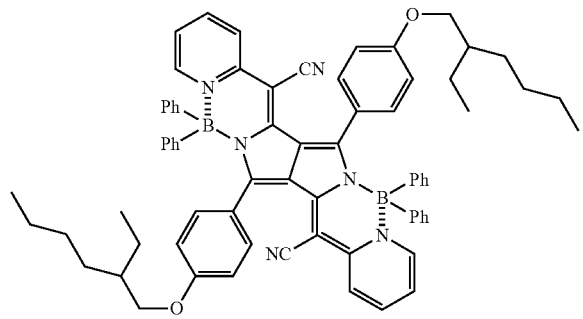
D-26
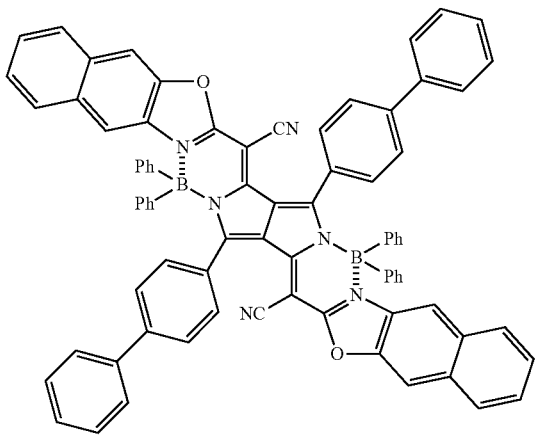

-continued
D-27
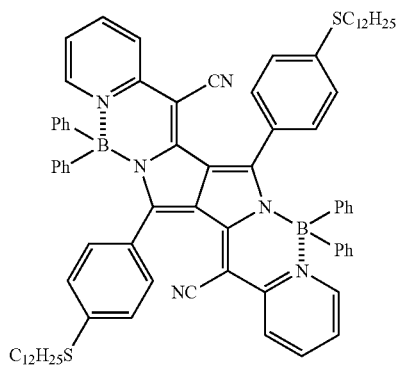
D-28
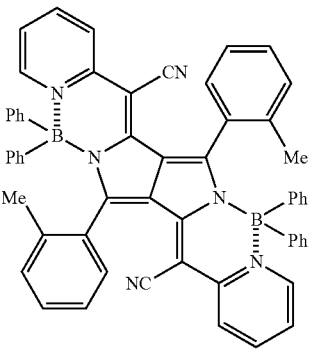
D-29
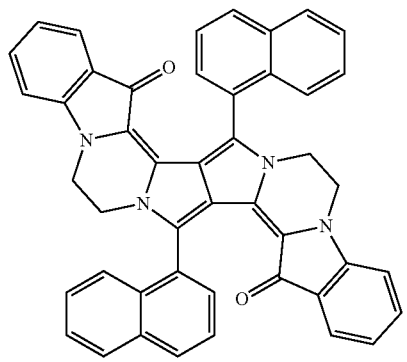
D-30
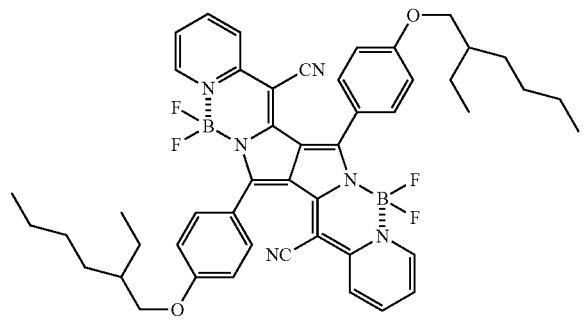
D-31
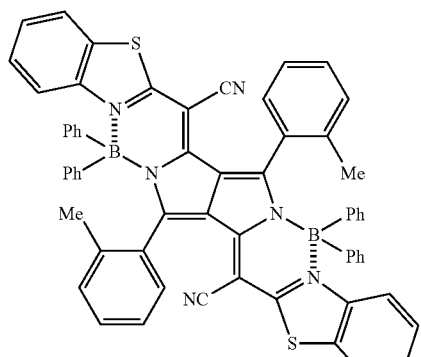
D-32
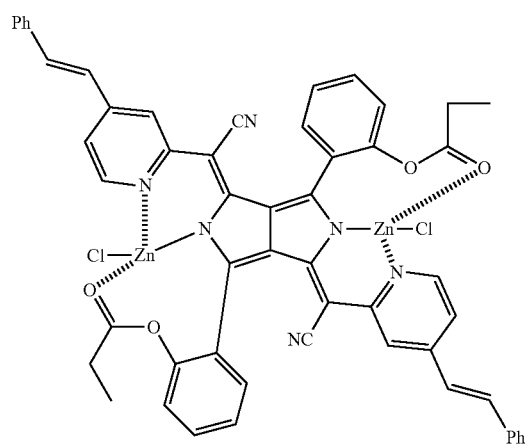
[Chemical formula 13]
D-33
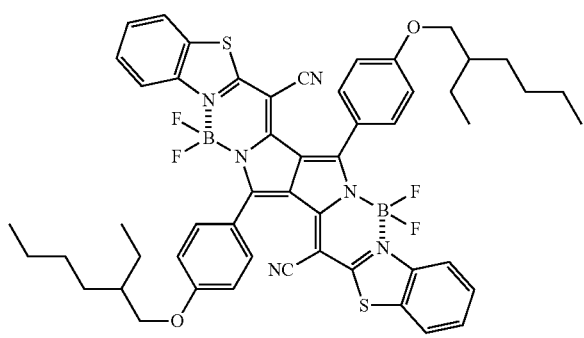
D-34
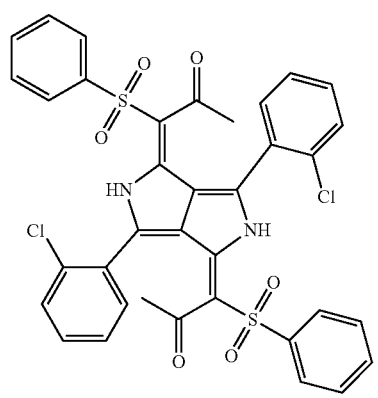

-continued
D-35
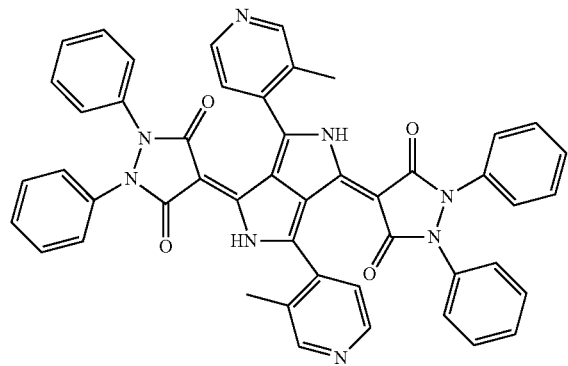
D-36
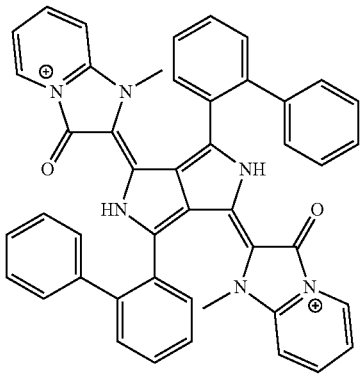
D-37
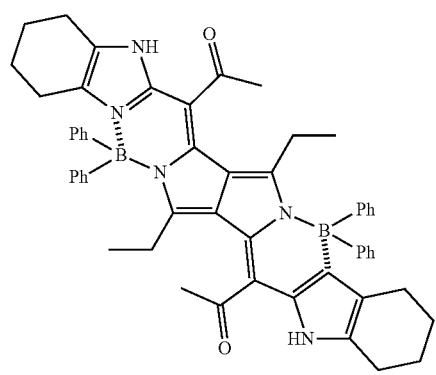
D-38
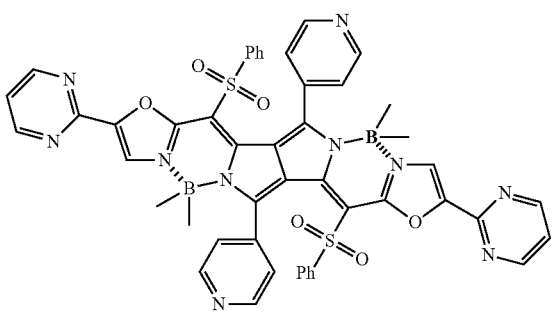
D-39
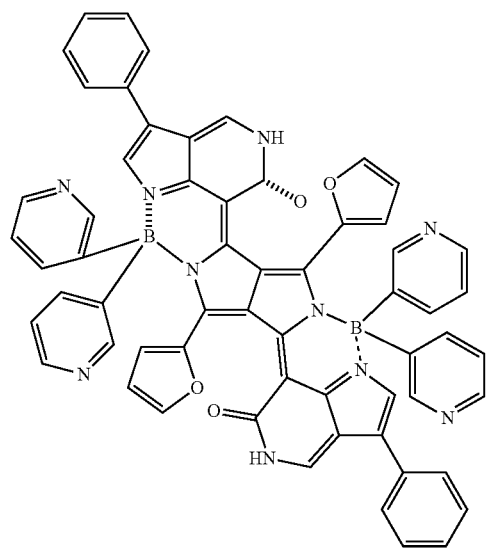
D-40
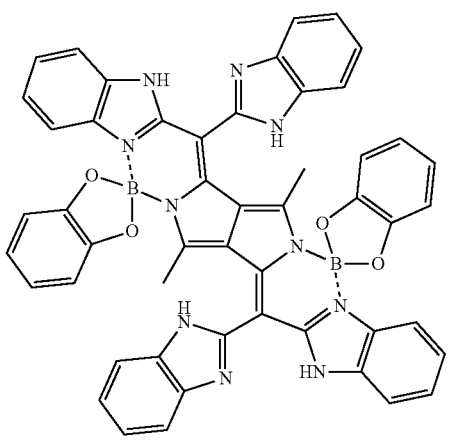

D-39
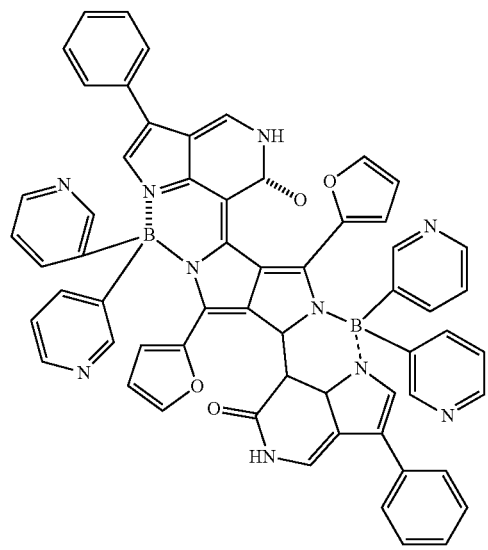
D-40
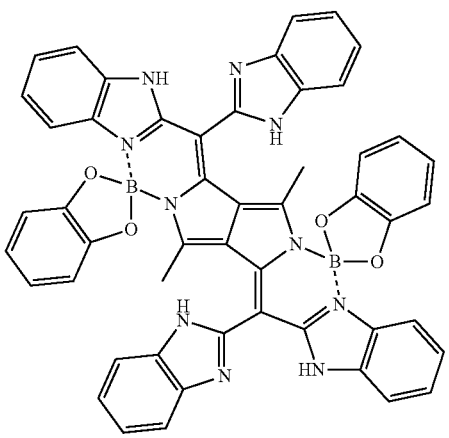
[Chemical formula 14]
D-41
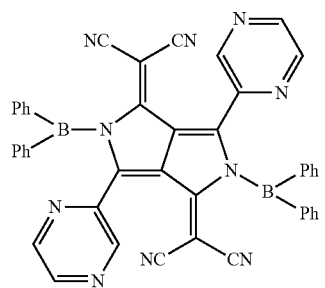
D-42
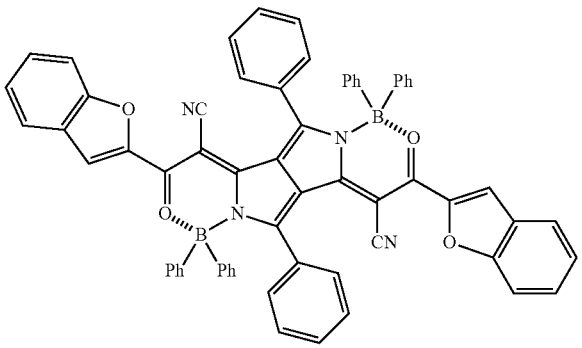
D-43
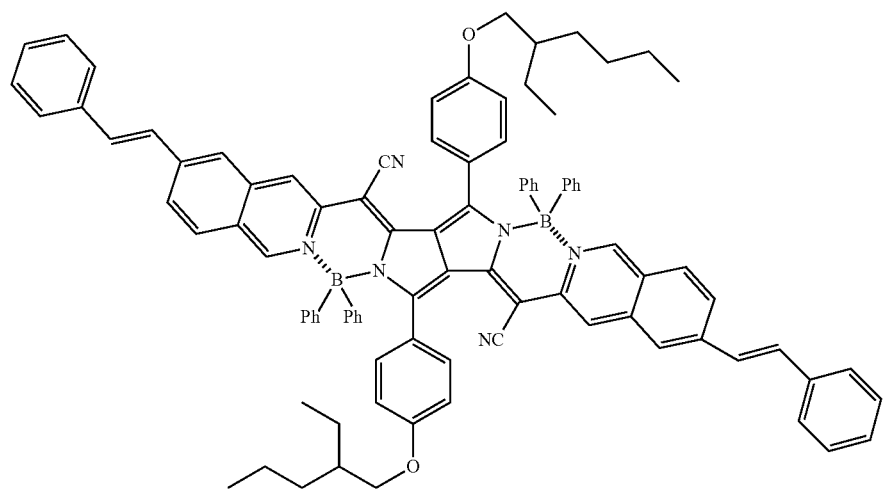

-continued
D-44
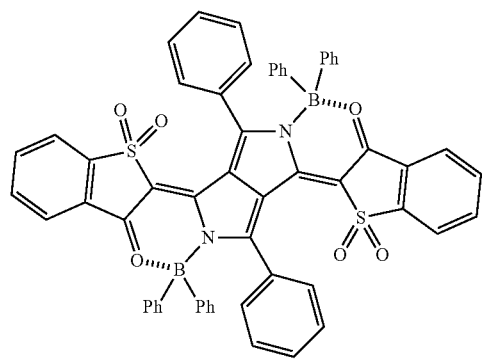
D-45
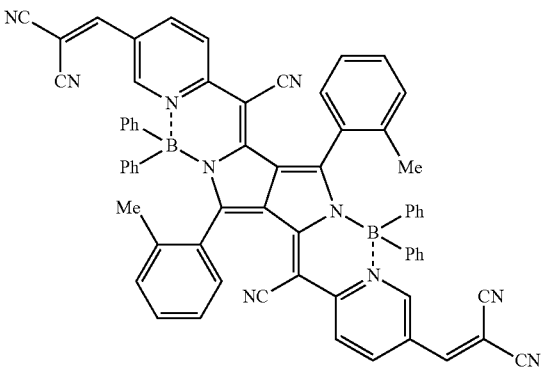
D-46
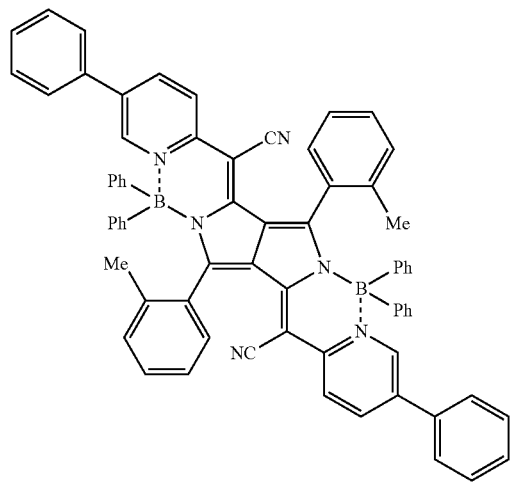
D-47
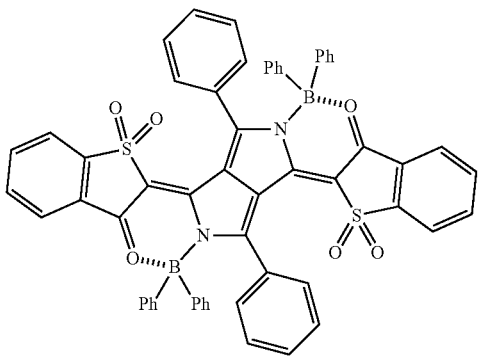
[Chemical formula 15]
D-101
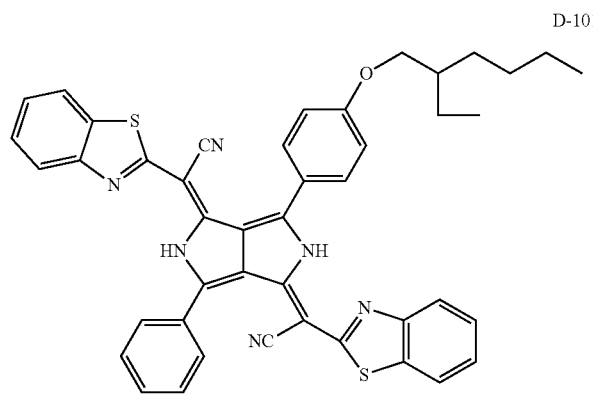
D-102
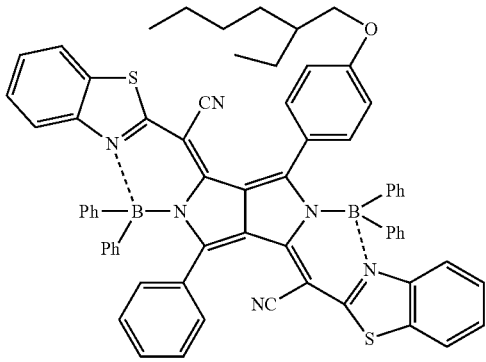
D-103
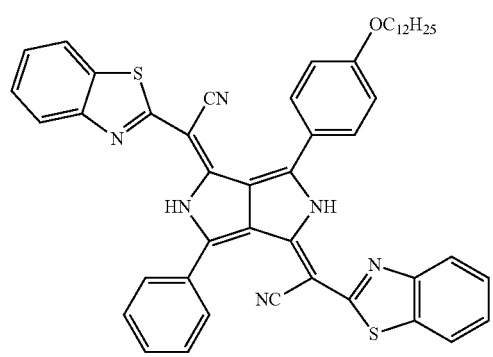
D-104
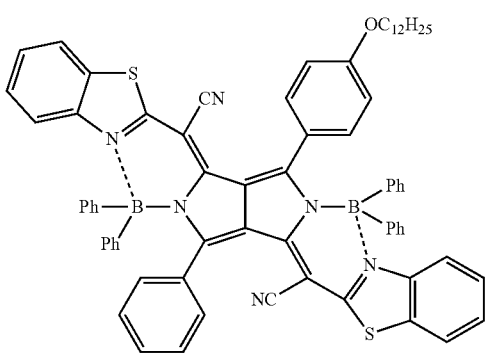

-continued
D-105
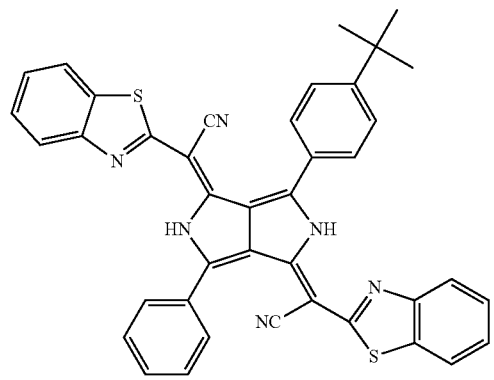
D-106
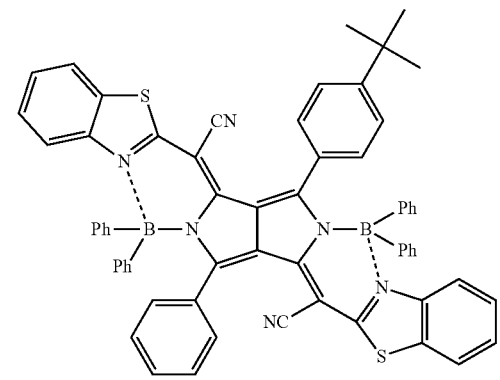
D-107
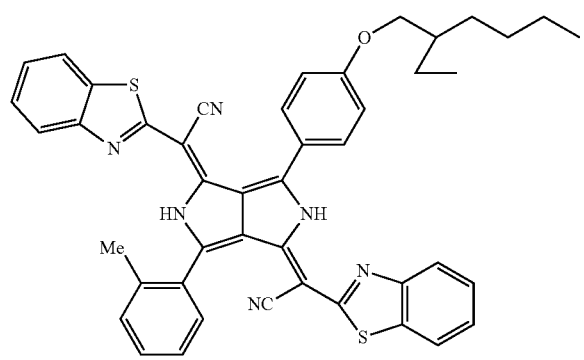
D-108
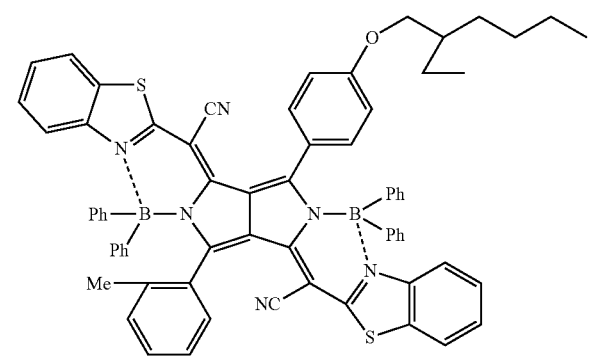
D-109
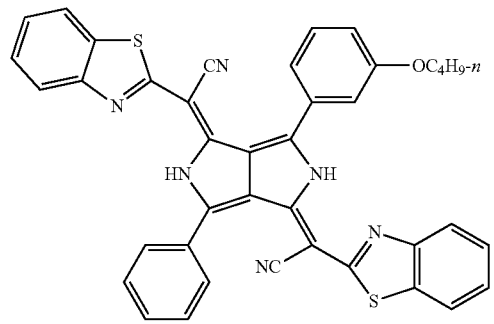
D-110
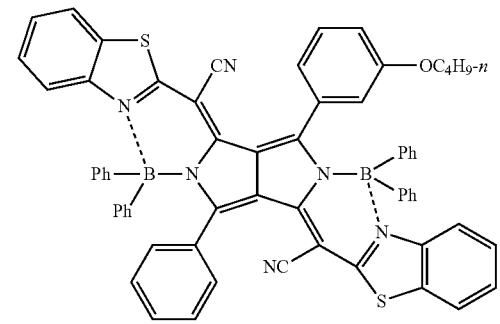
[Chemical formula 16]
D-111
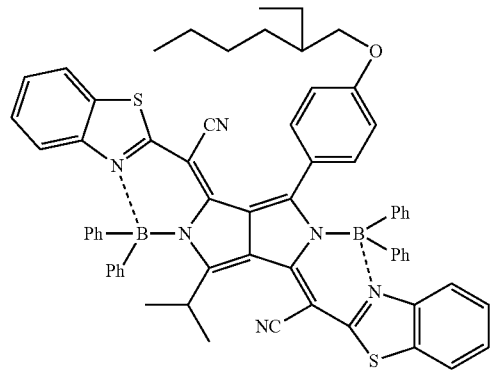
D-112
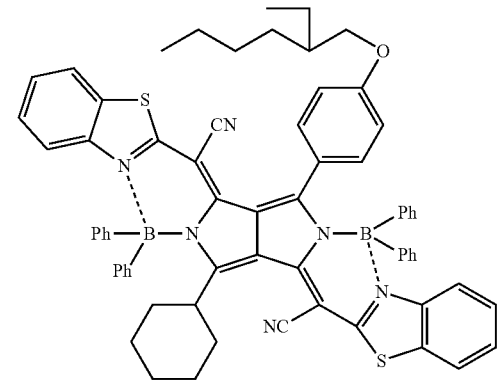

-continued
D-113
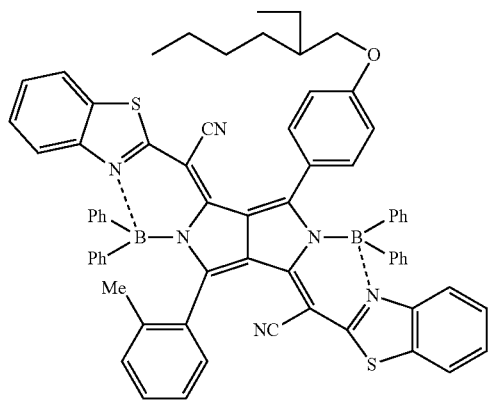
D-114
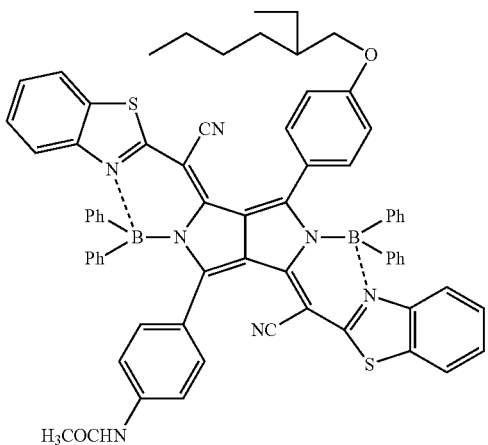
D-115
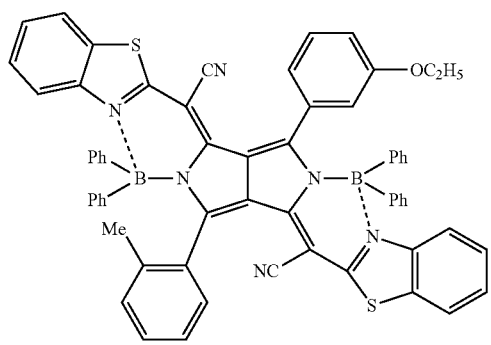
D-116
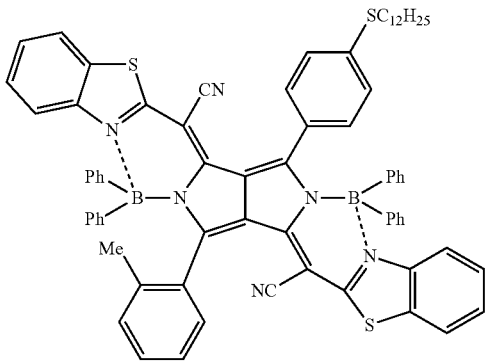
D-117
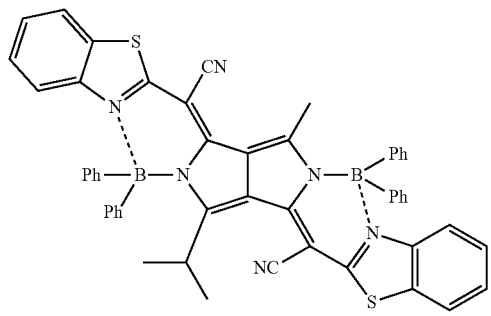
D-118
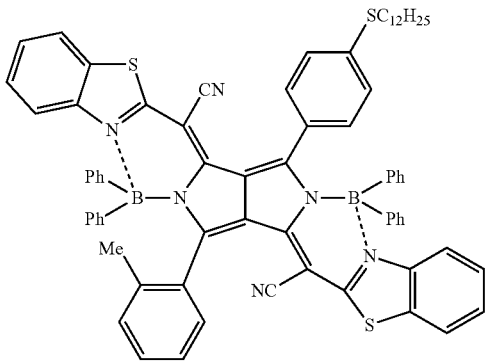
D-119
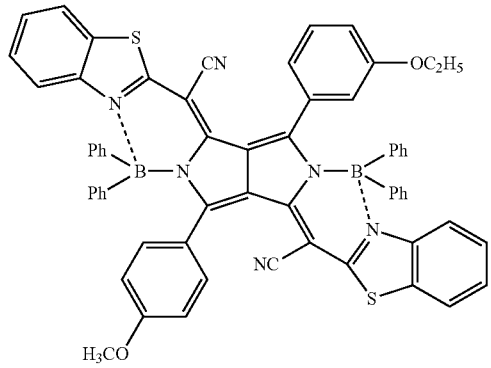
D-120
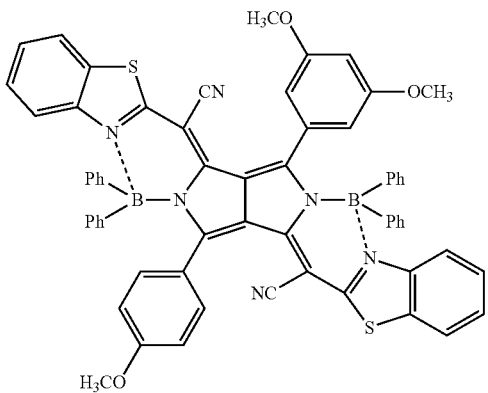

[Chemical formula 17]
D-121
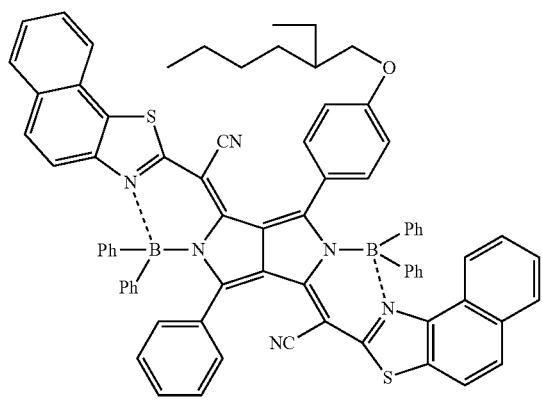
D-122
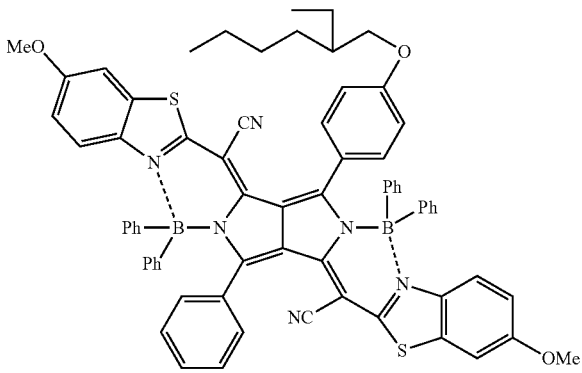
D-123
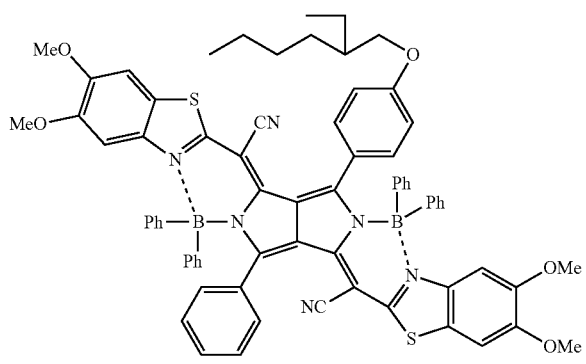
D-124
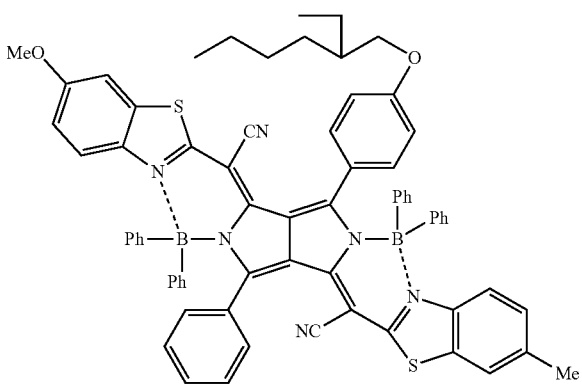
D-125
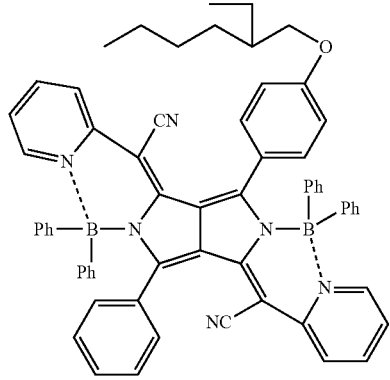
D-126
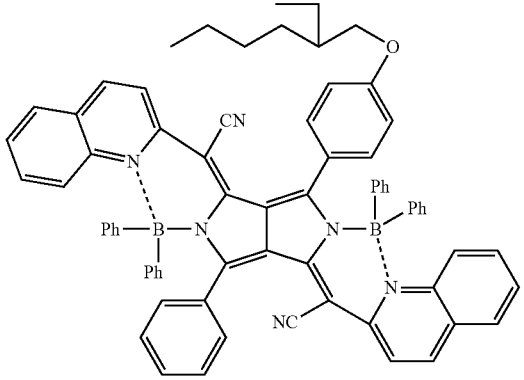
D-127
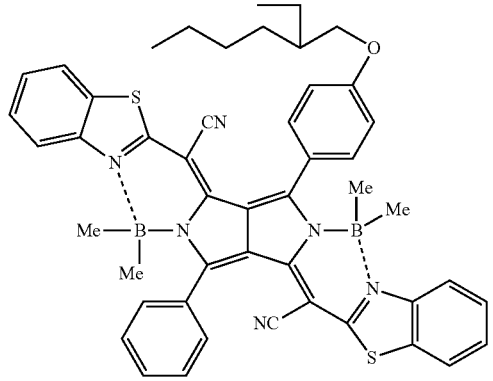
D-128
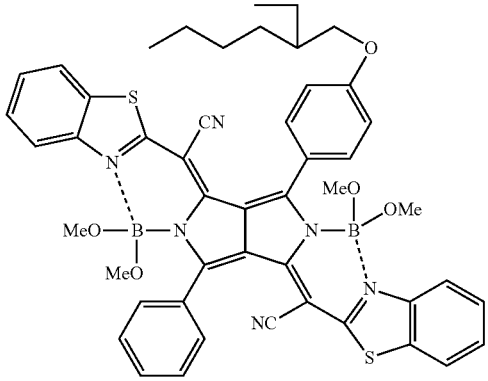

-continued
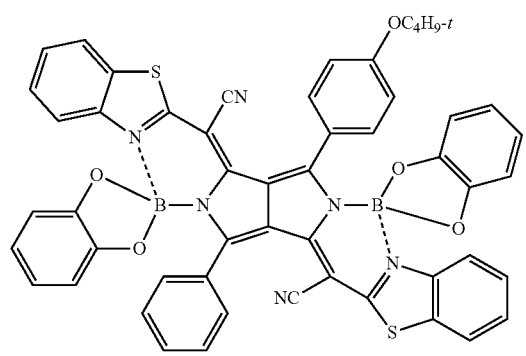
D-129
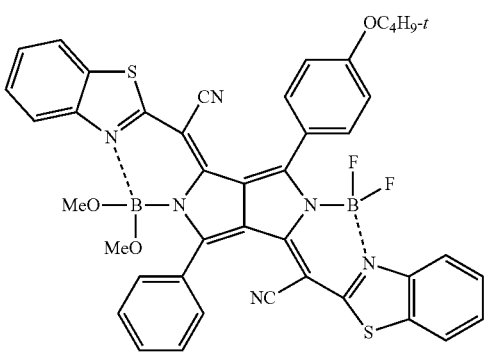
D-130
[Chemical formula 18]
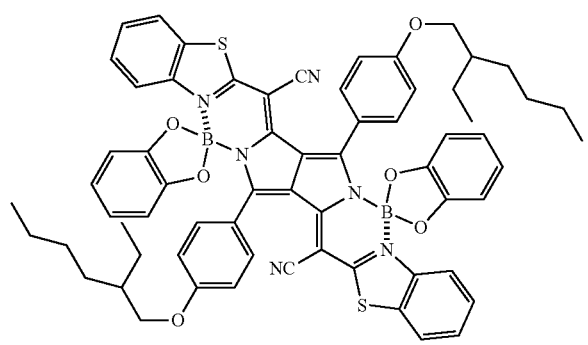
D-131
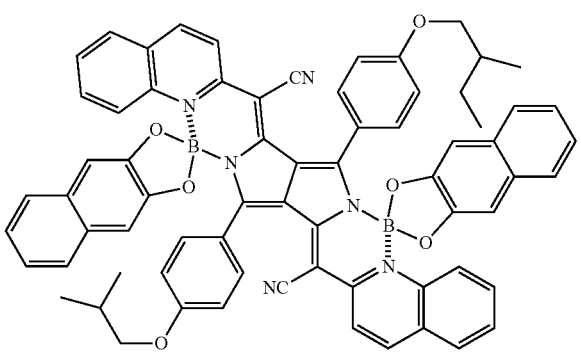
D-132
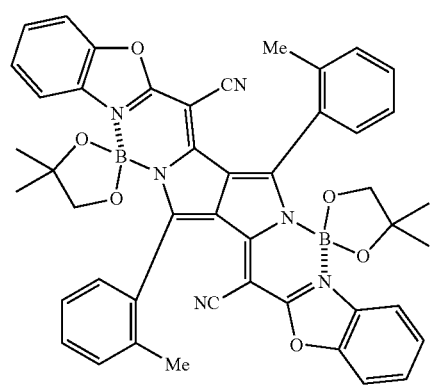
D-133
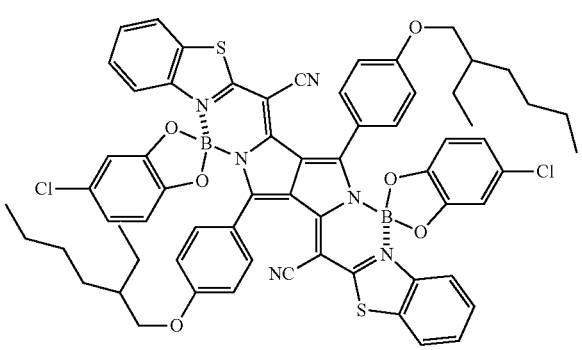
D-134

-continued
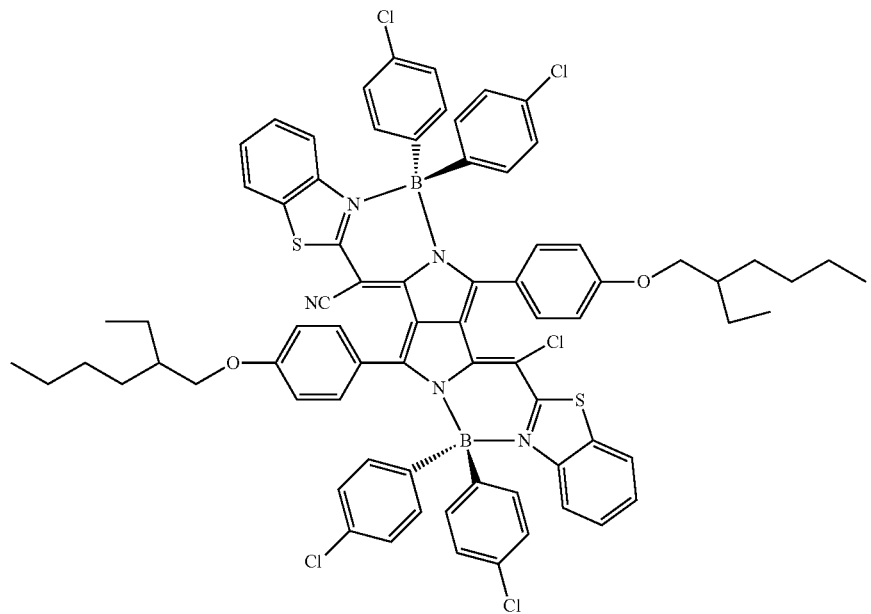
D-135
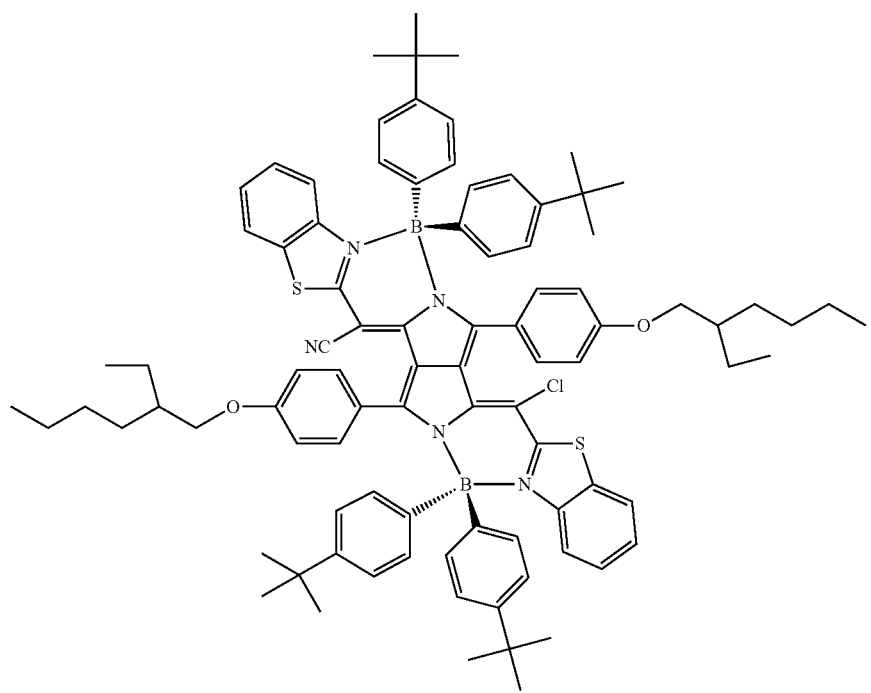
D-136

-continued

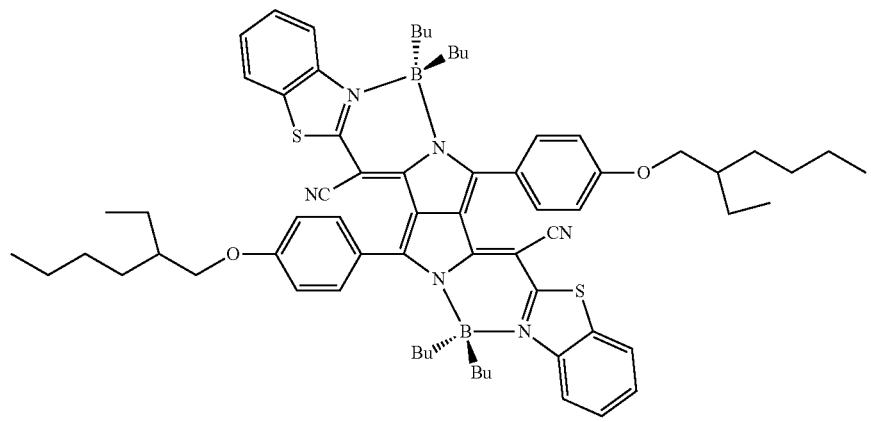

D-137

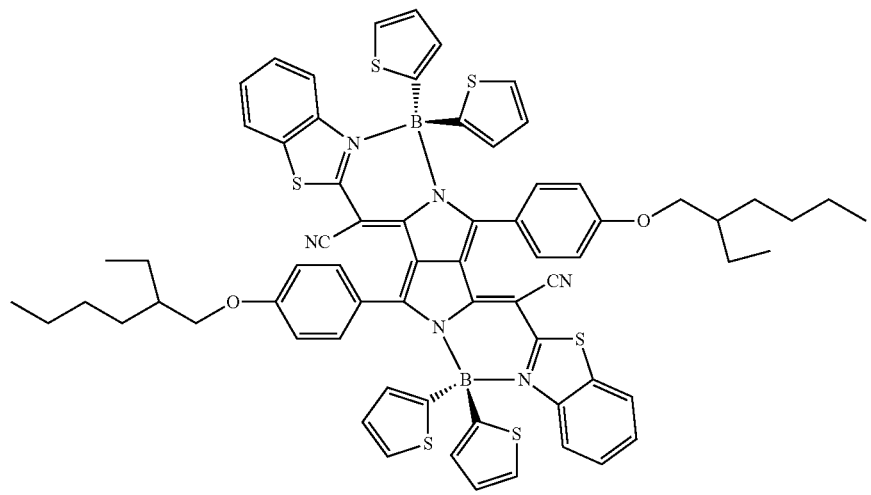

D-138

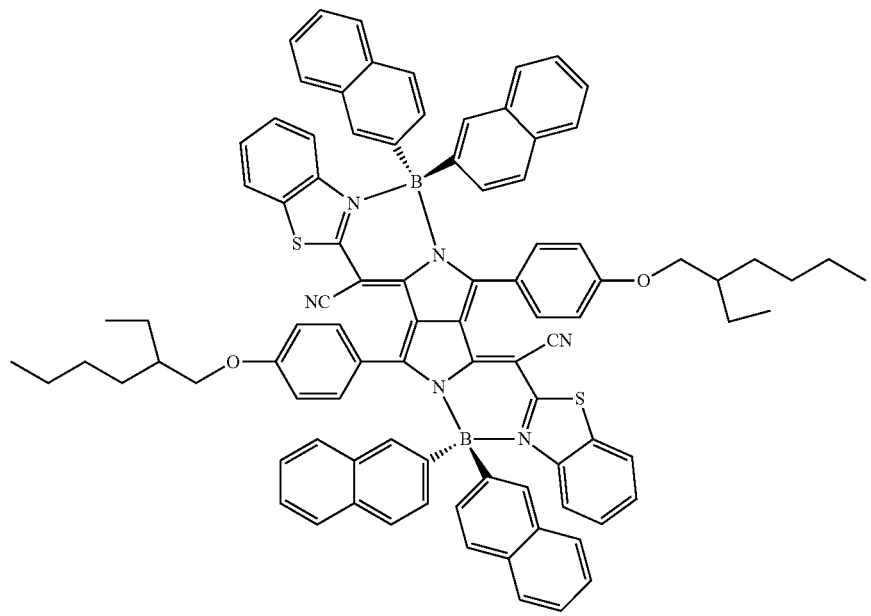

D-139

Hereinafter, a method for synthesizing the compound represented by any one of formulae (1) to (4) will be described.

The compound represented by any one of formulae (1) to (4) may be synthesized by condensing an active methylene compound with the corresponding diketopyrrolopyrrole compound and, as the case may be, further causing the resultant to react with a boron or a metal. The diketopyrrolopyrrole compound may be synthesized by a method described on pages 160 to 163 of "High Performance Pigments", Wiley-VCH, 2002. More specifically, the compound may be synthesized by a method in U.S. Pat. No. 5,969,154 or JP-A-9-323993. The condensation reaction between the diketopyrrolopyrrole compound and the active methylene compound or the subsequent boronization may be attained in accordance with the description of the above-described Non-Patent Document 1, Angewante Chemie International Edition of English, vol. 46, pp. 3750-3753 (2007). A reagent for the boronization may be synthesized with reference to J. Med. Chem. vol. 3, pp. 356-360 (1976). For example, bromocatechol borane may be commercially available from Tokyo Chemical Industry Co., Ltd.

The compound represented by any one of formulae (1) to (4) have the absorption maximum of preferably from 700 to 1050 nm, more preferably from 700 to 1,000 nm, though it is not particularly limited. It is preferable that the compound represented by any one of formulae (1) to (4) selectively absorbs infrared rays having a wavelength of 700 nm or more and 1,000 nm or less.

The compound represented by any one of formulae (1) to (4) have the molar absorption coefficient ε of preferably from 50,000 to 300,000, more preferably from 100,000 to 250,000, though it is not particularly limited.

The compound represented by any one of formulae (1) to (4) can be preferably used as an IR dye. Since the compound should be invisible, the compound is preferably transparent. However, the compound may be colored into slight green or gray.

The fine particle of the present invention comprises the compound represented by formula (1).

The particle diameter of the fine particle of the present invention is preferably 1 nm or more and 1000 nm or less, more preferably 5 nm or more and 600 nm or less, and particularly preferably 20 nm or more and 200 nm or less. In the present invention, the particle diameter can be measured by nano-track UPA particle diameter analyzer by using Dynamic Light Scattering (trade name: UPA-EX150, manufactured by Nikkiso Co., Ltd.) and the like.

The preparation method of the fine-particles using any one of the compounds represented by formulae (1) to (4) is explained below.

[Preparation Method of Fine Particle]

The compound represented by any one of the above-described formulae (1) to (4) can be obtained as a crude crystal by the above-described synthetic method. When the crude crystal is used as a fine particle of the present invention, the crude crystal is preferably subjected to a post treatment. Specifically, examples of the treatment include a milling treatment such as solvent salt milling, salt milling, dry milling, solvent milling, or acid pasting, a fine-particle-controlling treatment such as a solvent heating treatment, and a surface treatment with a resin, a surfactant, a dispersing agent, or the like.

The compound represented by any one of the above-described formulae (1) to (4) may be subjected to a solvent heating treatment as a post treatment. Examples of the solvent used in the solvent heating treatment include water; aromatic hydrocarbon solvents such as toluene and xylene; halogenated hydrocarbon solvents such as chlorobenzene and o-dichlorobenzene; alcohol solvents such as isopropanol and isobutanol; polar aprotic organic solvents such as N,N-dimethylformamide, N,N-dimethylacetamide and N-methyl-2-pyrrolidone, glacial acetic acid, pyridine, and a mixture of these solvents. It is preferred to adjust an average particle diameter of the dye in the range of from 0.01 μm to 1 μm by these post treatments.

[Composition]

The composition comprising the fine particle of the present invention may be an aqueous or non-aqueous composition. In the aqueous fine particle composition of the present invention, the aqueous liquid for dispersing the fine particle is mainly composed of water, and it is also possible to use a mixture of water as a main component and a hydrophilic organic solvent added on demand.

Examples of the hydrophilic organic solvent include alcohols (e.g., methanol, ethanol, propanol, iso-propanol, butanol, isobutanol, sec-butanol, t-butanol, pentanol, hexanol, cyclohexanol, and benzylalcohol), polyhydric alcohols (e.g., ethylene glycol, diethylene glycol, triethylene glycol, polyethylene glycol, propylene glycol, dipropylene glycol, polypropylene glycol, butylene glycol, hexanediol, pentanediol, glycerin, hexanetriol, and thiodiglycol), glycol derivatives (e.g., ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monoethyl ether, and ethylene glycol monophenyl ether), amines (e.g., ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, and tetramethylpropylenediamine), and other polar solvents (e.g., formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, and acetone).

Further, the aqueous fine particle composition of the present invention may contain an aqueous resin. Examples of the aqueous resin include a water-soluble resin which is dissolved in water, a water-dispersing resin which is dispersed in water, a colloidal dispersion resin and a mixture of these resins. Specific examples of the aqueous resin include acrylic resins, styrene-acrylic resins, polyester resins, polyamide resins, polyurethane resins, and fluorine resins.

(Water-Dispersing Resin which is Dispersed in Water)

The water-dispersing resin used in the present invention is dispersion in which a hydrophobic synthetic resin is dispersed in a dispersion medium whose main component is water. The aforementioned dispersion medium in which a main component is water may be referred to as a solvent in the present specification.

The water content by percentage in the solvent is preferably from 30 to 100% by mass, and more preferably from 50 to 100% by mass. The solvent other than water is preferably a solvent having a water-solubility, for example, alcohols such as methanol, ethanol or isopropyl alcohol, ketones such as acetone or methyl ethyl ketone, tetrahydrofuran, or butyl cellosolve.

As the synthetic resin (polymer), various kinds of polymers such as acrylic resins, styrene-acrylic resins, vinyl resins, polyurethane resins, polyester resins, polyamide resins and fluorine resins may be used. Further, examples of the water-soluble resin include gelatin, polyvinyl alcohol, and carboxymethyl cellulose.

Examples of the acrylic resin include a homopolymer of any monomer of acrylic acid, acrylate such as alkyl acrylate, acrylamide, acrylonitrile, methacrylic acid, methacrylate such as alkyl methacrylate, methacrylamide and methacrylonitrile, and a copolymer obtained through polymerization of two or more such monomers. Of those, preferred are a homopolymer of any monomer of acrylate such as alkyl acrylate and methacrylate such as alkyl methacrylate, and a copolymer obtained through polymerization of two or more such monomers. For example, they include a homopolymer of any monomer of acrylate and methacrylate having an alkyl group having 1 to 6 carbon atoms; and a copolymer obtained through polymerization of two or more such monomers. The acrylic resin is a polymer that comprises the above-mentioned composition as its essential ingredient and is obtained partly by the use of a monomer having any group of a methylol group, a hydroxyl group, a carboxyl group and an amino group so as to be crosslinkable with a carbodiimide compound.

Examples of the vinyl resin include polyvinyl alcohol, acid-modified polyvinyl alcohol, polyvinyl formal, polyvinyl butyral, polyvinyl methyl ether, polyolefin, ethylene/butadiene copolymer, polyvinyl acetate, vinyl chloride/vinyl acetate copolymer, vinyl chloride/(meth)acrylate copolymer and ethylene/vinyl acetate-based copolymer (preferably ethylene/vinyl acetate/(meth)acrylate copolymer). Of those, preferred are polyvinyl alcohol, acid-modified polyvinyl alcohol, polyvinyl formal, polyolefin, ethylene/butadiene copolymer, and ethylene/vinyl acetate-based copolymer (preferably ethylene/vinyl acetate/acrylate copolymer). The vinyl resins of polyvinyl alcohol, acid-modified polyvinyl alcohol, polyvinyl formal, polyvinyl butyral, polyvinyl methyl ether and polyvinyl acetate may be, for example, so designed that a vinyl alcohol unit is kept remaining in the polymer so that the polymer may have a hydroxyl group and is crosslinkable with a carbodiimide compound; and the other polymers may be modified, for example, partly by the use of a monomer having any group of a methylol group, a hydroxyl group, a carboxyl group and an amino group so that the polymer is crosslinkable with the compound.

Examples of the polyurethane resin include polyurethanes that are derived from at least any one of polyhydroxy compounds (e.g., ethylene glycol, propylene glycol, glycerin, trimethylolpropane), aliphatic polyester-type polyols obtained through reaction of polyhydroxy compounds and polybasic compounds, polyether polyols (e.g., poly(oxypropylene ether)polyol, poly(oxyethylene-propylene ether) polyol), polycarbonate-type polyols, and polyethylene terephthalate polyols, or their mixture; and a polyisocyanate. In the polyurethane resin, for example, the remaining hydroxyl group (i.e., unreacted) after the reaction of polyol and polyisocyanate may be utilized as a functional group crosslinkable with a carbodiimide compound.

Examples of the polyester resin include a polymer generally obtained through reaction of a polyhydroxy compound (e.g., ethylene glycol, propylene glycol, glycerin, trimethylolpropane) and a polybasic acid. In the polyester resin, for example, the remaining hydroxyl group or the carboxyl group (i.e., unreacted) after the reaction of the polyol and the polybasic acid may be utilized as a functional group crosslinkable with a carbodiimide compound. Needless-to-say, a third component having a functional group such as a hydroxyl group may be added to it.

The dispersed state of the aqueous dispersion of the polymer may be one in which the polymer is emulsified in a dispersion medium, one in which the polymer underwent emulsion polymerization, one in which the polymer underwent micelle dispersion, one in which the polymer molecules partially have a hydrophilic structure. The aqueous dispersion of the polymer (referred to singly as aqueous dispersion) is described in "Gosei Jushi Emulsion (Synthetic Resin Emulsion)", compiled by Taira Okuda and Hiroshi Inagaki, issued by Kobunshi Kanko Kai (1978); "Gosei Latex no Oyo (Application of Synthetic Latex)", compiled by Takaaki Sugimura, Yasuo Kataoka, Souichi Suzuki, and Keishi Kasahara, issued by Kobunshi Kanko Kai (1993); Soichi Muroi, "Gosei Latex no Kagaku (Chemistry of Synthetic Latex)", issued by Kobunshi Kanko Kai (1970); and so forth. The dispersed particles preferably have a mean particle size (diameter) of about 1 to 50,000 nm, more preferably about 5 to 1,000 nm. The particle size distribution of the dispersed particles is not particularly limited, and the particles may have either wide particle-size distribution or monodispersed particle-size distribution.

For the aqueous dispersion, commercially available polymers as described in the following may be used:

SUPER FLEX 830, 460, 870, 420, 420NS (polyurethanes manufactured by Dai-ichi Kogyo Seiyaku Co., Ltd.), BONDICK 1370NS and 1320NS, and HYDRAN Hw140SF, WLS201, WLS202, and WLS213 (polyurethanes manufactured Dainippon Ink & Chemicals, Inc.), OLESTER UD350, UD500, and UD600 (polyurethanes manufactured by Mitsui Chemicals, Inc.), NEOREZ R972, R966, and R9660 (polyurethanes manufactured by Kusumoto Chemicals, Ltd.), FINETEX Es650 and Es2200 (polyesters manufactured by Dainippon Ink & Chemicals, Inc.), VYLONAL MD1100, MD1400, and MD1480 (polyesters manufactured by Toyobo Co., Ltd.), JURIMAR ET325, ET410, AT-613, and SEK301 (acrylic resin manufactured by Nihon Junyaku Co., Ltd.), BONCOAT AN117, and AN226 (acrylic resin manufactured by Dainippon Ink & Chemicals, Inc.), LUCKSTAR DS616, DS807 (styrene-butadiene rubber manufactured by Dainippon Ink & Chemicals, Inc.), NIPPOL LX110, LX206, LX426, and LX433 (styrene-butadiene rubber manufactured by ZEON CORPORATION), and NIPPOL LX513, LX1551, LX550, and LX1571 (acrylonitrile-butadiene rubber manufactured by ZEON CORPORATION), each of which is a trade name.

As the polymer used in the binder of the composition of the present invention, a single kind thereof may be used alone or, if necessary, two or more kinds thereof may be used in a mixture form.

The molecular weight of the polymer used in the binder of the near-infrared absorptive layer is not particularly limited. Usually, the weight-average molecular weight is preferably from about 3,000 to about 1,000,000. If the weight-average molecular weight is too small, the composition may give a coated (or painted) layer insufficient in strength. If the molecular weight is too large, the composition may give a poor coating (or painted) surface state.

The dispersion quality of the fine-particles and the image quality may be improved by use of a surfactant and a dispersing agent. Examples of the surfactant include an anionic surfactant, a nonionic surfactant, a cationic surfactant, and an amphoteric surfactant. Any one of these surfactants may be used. Preferably, an anionic or nonionic surfactant is used.

Examples of the anionic surfactant include fatty acid salts, alkylsulfates, alkylbenzenesulfonates, alkylnaphthalenesulfonates, dialkylsulfosuccinates, alkyldiarylether disulfonates, alkylphosphates, polyoxyethylene alkylether sulfates, polyoxyethylene alkylarylether sulfates, naphthalenesulfonic acid/formalin condensates, polyoxyethylene alkylphosphates, glycerol borate fatty acid esters, and polyoxyethylene glycerol fatty acid esters.

Examples of the nonionic surfactant include polyoxyethylenealkyl ethers, polyoxyethylenealkylaryl ethers, polyoxyethyleneoxypropylene block copolymers, sorbitan fatty acid esters, polyoxyethylenesorbitan fatty acid esters, polyoxyethylenesorbitan fatty acid esters, glycerol fatty acid esters, polyoxyethylene fatty acid esters, polyoxyethylenealkylamines, fluorine-based surfactants, and silicon-based surfactants.

The non-aqueous fine particle composition is in the form in which the compound represented by any one of the above-described formulae (1) to (4) is dispersed in a non-aqueous vehicle. Examples of the resin used in the non-aqueous vehicle include petroleum resins, casein resins, shellack, rosin-modified maleic acid resins, rosin-modified phenol resins, nitrocellulose, celluloseacetatebutyrate, cyclized rubber, chlorinated rubber, oxidized rubber, hydrochlorinated rubber, phenol resins, alkyd resins, polyester resins, unsaturated polyester resins, amino resins, epoxy resins, vinyl resins, polyvinylchloride, vinyl chloride-vinyl acetate copolymer, acrylic resins, methacrylic resins, polyurethane resins, silicon resins, fluorine resins, drying oil, synthetic drying oil, styrene/maleic acid resins, styrene/acrylic resins, polyamide resins, polyimide resins, polyester resins, benzoguanamine resins, melamine resins, urea resins chlorinated polypropylene, butyral resins, vinylidene chloride resins. As the non-aqueous vehicle, a light curing resin or a heat curing resin may be used.

Examples of the solvent used in the non-aqueous vehicle include aromatic solvents such as toluene, xylene, and methoxybenzene; acetate solvents such as ethyl acetate, butyl acetate, propyleneglycol monomethylether acetate, and propyleneglycol monoethylether acetate; propionate solvents such as ethoxyethylpropionate; alcohol solvents such as methanol and ethanol; ether solvents such as butyl cellosolve, propyleneglycol monomethylether, diethyleneglycol ethylether, and diethyleneglycol dimethylether; ketone solvents such as methylethyl ketone, methylisobutyl ketone, and cyclohexanone; aliphatic hydrocarbon solvents such as hexane; nitrogen compound solvents such as N,N-dimethylformamide, γ-butyrolactam, N-methyl-2-pyrrolidone, aniline, and pyridine; lactone solvents such as γ-butyrolactone; and carbamic acid esters such as a mixture of methyl carbamate and ethyl carbamate having a mixture ratio of 48:52.

The composition of the present invention can be obtained by dispersing the compound represented by any one of the above-described formulae (1) to (4) and the aqueous or non-aqueous medium using a dispersing device. A dispersing device is, for example, a ball mill, a sand mill, a bead mill, a roll mill, a jet mill, a paint shaker, an attriter, an ultrasonic dispersing machine, or a Disper.

In the present invention, the volume-average particle diameter of the fine particles is preferably 10 nm or more and 250 nm or less. The volume-particle diameter of fine particles means the particle diameter of the fine particles themselves, or the following when an additive such as a dispersing agent adheres onto the fine particles: the particle diameter of the additive-adhering fine-particles.

In the present invention, nano-track UPA particle diameter analyzer (trade name: UPA-EX150, manufactured by Nikkiso Co., Ltd.) may be used for measuring the volume-average particle diameter of fine particles. The measurement is made by putting 3 mL of a fine-particle-dispersion into a measuring cell, and then making an operation in accordance with a predetermined measuring method. Viscosity and dispersed particle density as parameters to be input at the time of the measurement, ink viscosity and fine-particle density are used, respectively.

The volume-average particle diameter of the fine particles is more preferably 20 nm or more and 250 nm or less, and further preferably 30 nm or more and 230 nm or less. If the number-average particle diameter of the fine particles in the dispersion is too small, the storage stability may not be ensured. On the other hand, if the diameter is too large, the optical density may be lowered.

A concentration of the fine particle contained in the composition of the present invention is preferably in the range of from 1% by mass to 35% by mass, and more preferably in the range of from 2% by mass to 25% by mass. If the concentration is too low, a sufficient color density may not be obtained when the fine particle dispersion is singly used. If the concentration is too high, dispersion stability may be deteriorated.

Examples of intended use of the fine particle of the present invention include an image-recording material for forming an image, especially invisible image. Specific examples of the image-recording material include an inkjet process recording material and other materials such as a heat-sensitive recording material, a pressure-sensitive recording material, a recording material used for electrophotography, a transfer process silver halide photosensitive material, a printing ink, and a recording pen. Among these materials, an inkjet process recording material, a heat-sensitive recording material and a recording material used for electrophotography are preferable.

Further, the fine particle of the present invention is applicable to an infrared cut filter that is used for a solid-state image sensing device such as CCD or a display such as PDP. Further, the fine particle of the present invention is also applicable to a stain solution for dying a variety of fibers.

Further since the fine particle of the present invention, when handled in the molecular state, shows absorption in the near-infrared range that is excellent in body permeability, the fine particle is also adaptable to a diagnostic marker and photo dynamic therapy in addition to the intended use as described above.

EXAMPLES

The present invention will be described in more detail based on the following examples. It is therefore understood that the present invention is by no means intended to be limited to the specific examples below. In the following examples and comparative examples, the term "part(s)" denote "part(s) by mass", unless otherwise specified.

Example 1
Preparation of Exemplified Compound (D-1)
An exemplified compound (D-1) was prepared in accordance with the following scheme.
[Chemical formula 19]
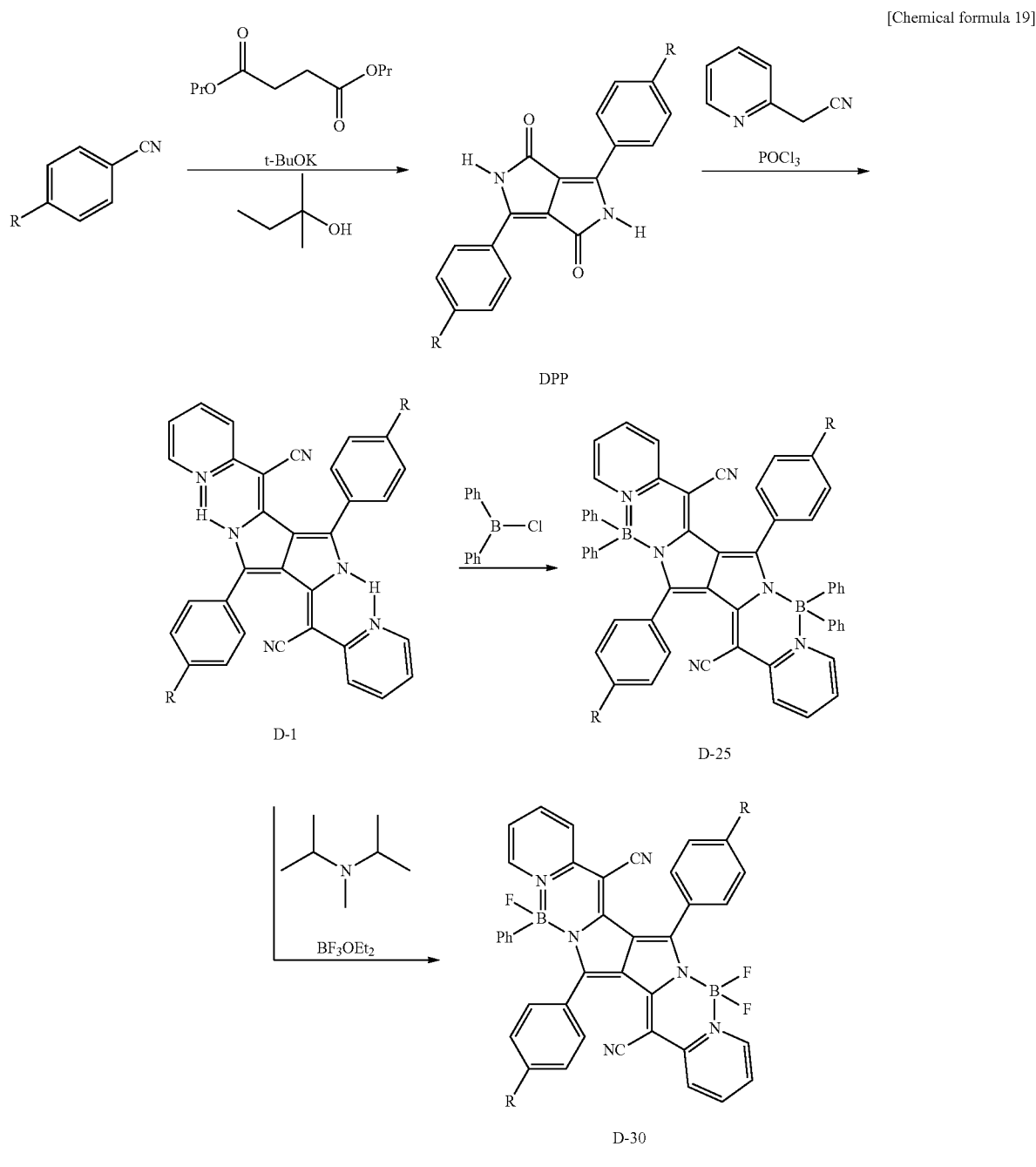
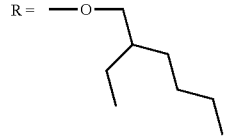

First, a diketopyrrolopyrrole compound (DPP) was synthesized in accordance with a method described in U.S. Pat. No. 5,969,154, using 4-(2-ethylhexyloxy)benzonitrile as a starting material.

In 60 mL of toluene, 3 g (1 equivalent by mol) of the diketopyrrolopyrrole compound, and 1.6 g (2.5 equivalents by mol) of pyridineacetonitrile were stirred, and then thereto was added 6.5 g (8 equivalents by mol) of phosphorus oxychloride. The solution was heated and refluxed for 4 hours. The solution was cooled to room temperature, and then thereto were added 50 mL of chloroform and 20 mL of water. Furthermore, the solution was stirred for 30 minutes. Therefrom, the organic layer was taken out by a liquid-separating operation. The organic layer was washed with an aqueous sodium hydrogen carbonate solution, and then the solvent was distilled off under reduced pressure. The obtained crude product was purified by silica gel column chromatography (solvent: chloroform), and further a chloroform/acetonitrile solvent was used to recrystallize the purified product to yield 3 g of the target compound (D-1) (yield: 77%).

$^1$H-NMR (CDCl$_3$): δ0.9-1.0 (m, 12H), 1.3-1.6 (m, 16H), 1.8 (m, 2H), 3.95 (d, 4H), 7.0 (t, 2H), 7.1 (d, 4H), 7.6 (m, 4H), 7.7 (d, 4H), 8.45 (d, 2H)

Example 2

Preparation of Exemplified Compound (D-25)

An exemplified compound (D-25) was prepared in accordance with the following scheme.

In 20 mL of o-dichlobenzene, 0.75 g (1 equivalent by mol) of the exemplified compound (D-1) and 0.5 g (2.5 equivalents by mol) of chlorodiphenyl borone were heated and refluxed for 3 hours. The solution was cooled to room temperature, and then thereto were added 10 mL of water. Therefrom, the organic layer was taken out by a liquid-separating operation. The organic layer was washed with an aqueous sodium hydrogen carbonate solution, and then the solvent was distilled off under reduced pressure. The obtained crude product was purified by silica gel column chromatography (solvent: chloroform), and further a chloroform/methanol solvent was used to recrystallize the purified product to yield 0.58 g of the target compound (D-25) (yield: 53%).

$^1$H-NMR (CDCl$_3$): δ0.9-1.0 (m, 12H), 1.3-1.6 (m, 16H), 1.8 (m, 2H), 3.75 (d, 4H), 6.35 (d, 4H), 6.65 (d, 4H), 6.7 (t, 2H), 7.1-7.2 (m, 20H), 7.35 (d, 2H), 7.45 (t, 2H), 7.8 (d, 2H)

Example 3

Preparation of Exemplified Compound (D-30)

An exemplified compound (D-30) was prepared in accordance with the following scheme.

In 20 mL of o-dichlobenzene, 1 g (1 equivalent by mol) of the exemplified compound (D-1) and 0.5 g (2.5 equivalents by mol) of borone trifluoride diethylether complex were heated and refluxed for 1 hour, and then thereto was added 0.75 g (5 equivalents by mol) of diisopropylmethylamine. The solution was further heated and refluxed for 1 hour. The solution was cooled to room temperature, and then thereto were added 10 mL of water. Therefrom, the organic layer was taken out by a liquid-separating operation. The solvent was distilled off under reduced pressure. The obtained crude product was purified by silica gel column chromatography (solvent: chloroform), and further a chloroform/methanol solvent was used to recrystallize the purified product to yield 0.8 g of the target compound (D-30) (yield: 70%).

$^1$H-NMR (CDCl$_3$): δ0.9-1.0 (m, 12H), 1.3-1.6 (m, 16H), 1.8 (m, 2H), 3.95 (d, 4H), 7.05 (d, 4H), 7.6 (d, 4H), 7.7 (t, 2H), 7.85 (t, 2H), 8.35 (d, 2H)

Example 4

Following exemplified compounds were prepared in the same manner as Example 1, except that the starting materials were changed. $^1$H-NMR results for identifying the structure thereof are shown below.

Exemplified Compound (D-2)

$^1$H-NMR (CDCl$_3$): 0.9 (t, 6H), 1.25-1.45 (m, 16H), 1.7 (m, 4H), 2.75 (t, 4H), 7.0 (t, 2H), 7.4 (d, 4H), 7.6 (d, 4H), 7.65 (m, 4H), 8.45 (d, 2H)

Exemplified Compound (D-3)

$^1$H-NMR (CDCl$_3$): 0.9 (t, 6H), 1.2-1.6 (m, 36H), 1.7 (m, 4H), 3.15 (m, 4H), 7.0 (t, 2H), 7.4-7.5 (m, 4H), 7.55-7.7 (m, 4H), 8.5 (d, 2H)

Exemplified Compound (D-4)

$^1$H-NMR (CDCl$_3$): 2.5 (s, 6H), 7.0 (m, 2H), 7.35-7.45 (m, 4H), 7.5 (t, 4H), 7.5 (m, 4H), 8.4 (d, 2H)

Exemplified Compound (D-9)

$^1$H-NMR (CDCl$_3$): 2.5 (s, 6H), 7.3 (m, 2H), 7.4-7.5 (m, 6H), 7.55 (m, 2H), 7.65 (d, 2H), 7.8 (m, 4H)

Exemplified Compound (D-10)

$^1$H-NMR (CDCl$_3$): δ0.9-1.0 (m, 12H), 1.35-1.6 (m, 16H), 1.8 (m, 2H), 3.85 (d, 4H), 6.45 (s, 8H), 7.0 (d, 4H), 7.15 (m 12H), 7.2 (m, 2H), 7.25 (m, 4H+4H), 7.5 (m, 2H)

Exemplified Compound (D-15)

$^1$H-NMR (CDCl$_3$): δ0.9-1.1 (m, 12H), 1.4-1.6 (m, 16H), 1.85 (m, 2H), 4.0 (d, 4H), 7.15 (d, 4H), 7.4 (m 4H), 7.6 (t, 2H), 7.75 (d, 4H), 7.8-7.9 (m, 6H)

Exemplified Compound (D-17)

$^1$H-NMR (CDCl$_3$): δ0.9-1.0 (m, 12H), 1.35-1.6 (m, 16H), 1.8 (m, 2H), 3.95 (d, 4H), 7.1 (d, 4H), 7.4-7.5 (m, 4H), 7.7 (d, 4H), 7.75 (d, 2H), 8.0 (d, 2H)

Exemplified Compound (D-21)

$^1$H-NMR (CDCl$_3$): δ1.0 (m, 12H), 1.4-1.55 (m, 16H), 1.8 (m, 2H), 3.85 (d, 4H), 6.5 (s, 8H), 7.1 (d, 2H), 7.15 (m, 12H), 7.3 (m, 4H+4H), 7.4 (d, 4H), 7.5 (m, 2H), 7.7 (t, 4H)

Exemplified Compound (D-28)

$^1$H-NMR (CDCl$_3$): 1.9 (s, 6H), 6.65 (d, 2H), 6.7-6.8 (m, 6H), 6.95 (m, 8H), 7.0-7.1 (m, 4H), 7.25-7.35 (m, 12H), 7.5 (m, 2H), 7.85 (d, 2H)

Exemplified Compound (D-31)

$^1$H-NMR (CDCl$_3$): 1.7 (s, 6H), 6.45 (t, 2H), 6.75-7.0 (m, 16H), 7.0-7.15 (m, 4H), 7.2-7.35 (m, 8H), 7.5 (m, 4H), 7.6 (d, 2H)

Exemplified Compound (D-33)

$^1$H-NMR (CDCl$_3$): δ0.9-1.0 (m, 12H), 1.35-1.55 (m, 16H), 1.8 (m, 2H), 3.95 (d, 4H), 7.1 (d, 4H), 7.35-7.5 (m, 4H), 7.7 (d, 4H), 7.75 (m, 2H), 8.0 (m, 2H)

Example 5

Preparation of Exemplified Compound (D-101)

An exemplified compound (D-101) was prepared in accordance with the following scheme.

[Chemical formula 20]

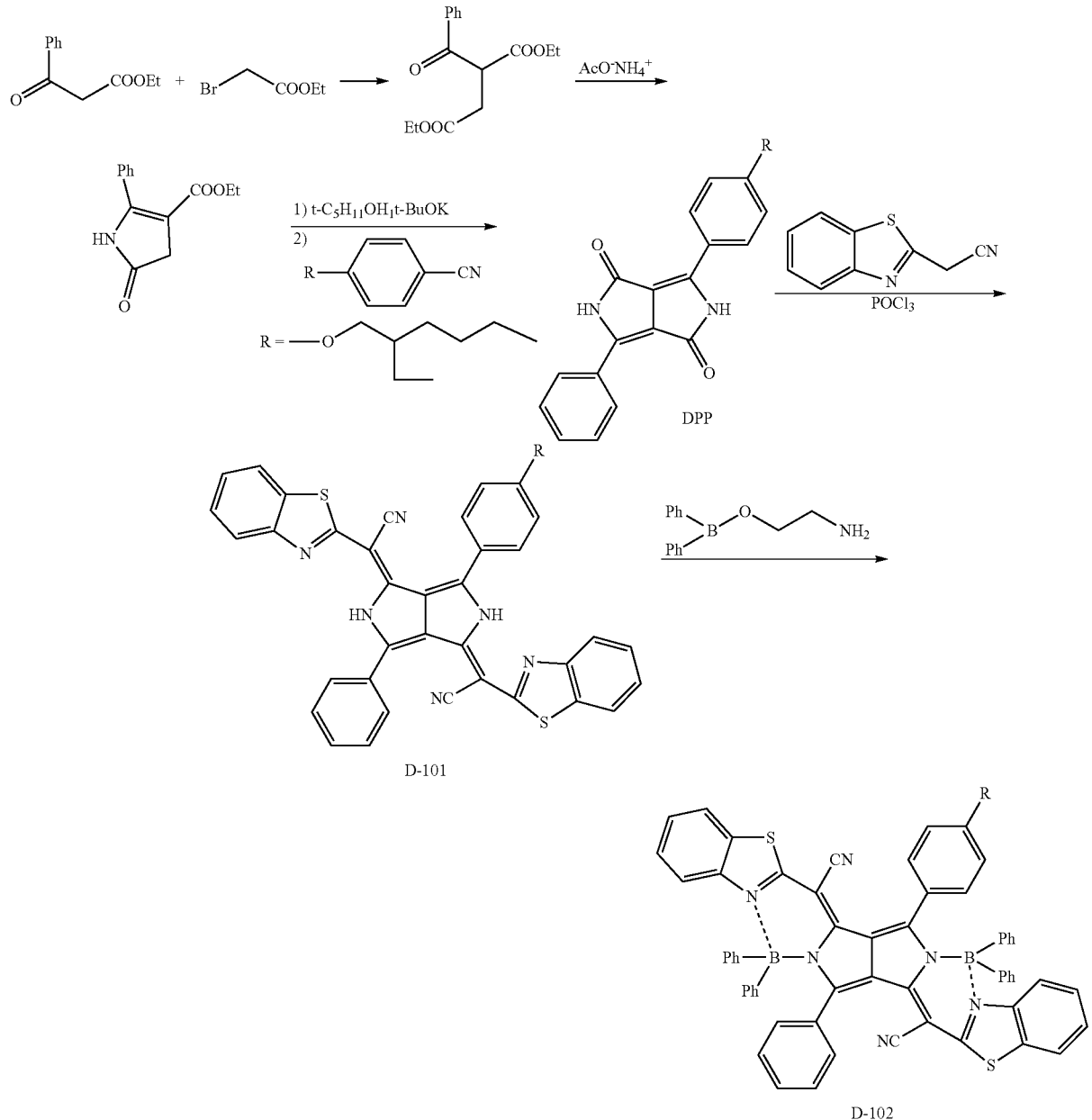

First, a diketopyrrolopyrrole compound (DPP) was synthesized in accordance with a method described in "Tetrahedron", 58, (2002), p. 5547-5565.

In 10 mL of o-dichlobenzene, 0.5 g (1 equivalent by mol) of the diketopyrrolopyrrole compound (DPP) and 0.53 g (2.5 equivalents by mol) of thiazole acetonitrile were stirred, and then thereto was added 0.9 ml of phosphorus oxychloride. The solution was heated and refluxed for 1 hour. The solution was cooled to room temperature, and then thereto were added 10 mL of chloroform and 5 mL of water. Furthermore, the solution was stirred for 30 minutes. Therefrom, the organic layer was taken out by a liquid-separating operation. The organic layer was washed with an aqueous sodium hydrogen carbonate solution, and then the solvent was distilled off under reduced pressure. Crystals obtained by addition of methyl alcohol were collected by filtration. Thus, 180 mg of the target compound (D-101) was obtained in yield of 28%.

The λmax of the exemplified compound (D-101) was 727 nm in chloroform. The molar absorption coefficient of the exemplified compound (D-101) was $9.77 \times 10^4$ dm$^3$/mol·cm in chloroform.

¹H-NMR (CDCl₃): δ0.9-1.0 (m, 6H), 1.3-1.6 (m, 8H), 1.8 (m, 1H), 3.85 (d, 2H), 7.1 (d, 2H), 7.3 (m, 2H), 7.4 (m, 2H), 7.6 (m, 3H), 7.7-7.8 (m, 8H)

Example 6

Preparation of Exemplified Compound (D-102)

An exemplified compound (D-102) was prepared in accordance with the following scheme.

In 4 mL of toluene, 0.18 g (1 equivalent by mol) of the exemplified compound (D-101), 0.125 g (2.2 equivalents by mol) of diphenyl borinic acid 2-aminoethyl ester and 0.19 g of titanium tetrachloride were heated and refluxed for 1 hour. The solution was cooled to room temperature, and then thereto were added 5 mL of methyl alcohol. Thereafter, crystals were collected by filtration. The obtained crude product was purified by silica gel column chromatography (solvent: chloroform) to yield 0.2 g of the target compound (D-102) (yield: 77%).

The λmax of the exemplified compound (D-102) was 780 nm in chloroform. The molar absorption coefficient of the exemplified compound (D-102) was $2.15 \times 10^5$ dm³/mol·cm in chloroform.

¹H-NMR (CDCl₃): δ0.9-1.0 (m, 6H), 1.3-1.6 (m, 8H), 1.8 (m, 1H), 3.8 (d, 2H), 6.4 (s, 4H), 6.5 (d, 2H), 7.0 (m, 6H), 7.1-7.2 (m, 15H), 7.3 (m, 8H), 7.5 (d, 2H)

Example 7

Preparation of Exemplified Compound (D-106)

First, an exemplified compound (D-105) was prepared in the same manner as Example 1, except that the starting materials were changed.

Next, in 4 mL of toluene, 0.15 g (1 equivalent by mol) of the exemplified compound (D-105), 0.11 g (2.2 equivalents by mol) of diphenyl borinic acid 2-aminoethyl ester and 0.17 g of titanium tetrachloride were heated and refluxed for 1 hour. The solution was cooled to room temperature, and then thereto were added 5 mL of methyl alcohol. Thereafter, crystals were collected by filtration. The obtained crude product was purified by silica gel column chromatography (solvent: chloroform) to yield 0.1 g of the target compound (D-106) (yield: 45%).

The λmax of the exemplified compound (D-106) was 779 nm in chloroform. The molar absorption coefficient of the exemplified compound (D-106) was $2.24 \times 10^5$ dm³/mol·cm in chloroform.

¹H-NMR (CDCl₃): δ1.3 (s, 9H), 6.5 (m, 4H), 6.9-7.0 (m, 8H), 7.1-7.2 (m, 14H), 7.2-7.3 (m, 9H), 7.5 (d, 2H)

Example 8

Preparation of Exemplified Compound (D-107)

An exemplified compound (D-107) was prepared in the same manner as Example 1, except that the starting materials were changed.

The λmax of the exemplified compound (D-107) was 727 nm in chloroform. The molar absorption coefficient of the exemplified compound (D-107) was $8.14 \times 10^4$ dm³/mol·cm in chloroform.

Example 9

Preparation of Exemplified Compound (D-108)

In 10 mL of toluene, 0.71 g (1 equivalent by mol) of the exemplified compound (D-107), 0.48 g (2.2 equivalents by mol) of diphenyl borinic acid 2-aminoethyl ester and 0.72 g of titanium tetrachloride were heated and refluxed for 1 hour. The solution was cooled to room temperature, and then thereto were added 10 mL of methyl alcohol. Thereafter, crystals were collected by filtration. The obtained crude product was purified by silica gel column chromatography (solvent: chloroform) to yield 0.7 g of the target compound (D-108) (yield: 70%).

The λmax of the exemplified compound (D-108) was 779 nm in chloroform. The molar absorption coefficient of the exemplified compound (D-108) was $1.94 \times 10^5$ dm³/mol·cm in chloroform.

¹H-NMR (CDCl₃): δ0.9-1.0 (m, 6H), 1.3-1.6 (m, 8H), 1.8 (m, 1H), 3.8 (s, 3H), 3.85 (d, 2H), 6.5 (s, 8H), 7.0 (m, 4H), 7.1-7.2 (m, 14H), 7.3 (m, 8H), 7.5 (d, 2H)

Example 10

Preparation of Exemplified Compound (D-131)

In 20 mL of toluene, 2.6 g (1 equivalent by mol) of the exemplified compound (D-17) and 2.4 g (4 equivalents by mol) of bromocatechol borane (manufactured by TOKYO KASEI KOGYO CO., LTD) were heated and refluxed for 3 hours. After cooling to room temperature, 20 mL of methanol was added. Then, precipitated crystals were collected by filtration. The obtained crude product was purified by silica gel column chromatography (solvent: chloroform), and further a chloroform/methanol solvent was used to recrystallize the purified product to yield 2.3 g of the target compound (D-131) (yield: 70%).

¹H-NMR (CDCl₃): δ0.95-1.05 (m, 12H), 1.35-1.6 (m, 16H), 1.7-1.8 (m, 2H), 3.75 (d, 4H), 6.4 (m, 4H), 6.5-6.65 (m, 8H), 7.1 (d, 2H), 7.15-7.3 (m, 8H), 7.45 (t, 2H), 7.7 (d, 2H)

Example 11

Preparation of Exemplified Compound (D-138)

An exemplified compound (D-138) was prepared in accordance with the following scheme.

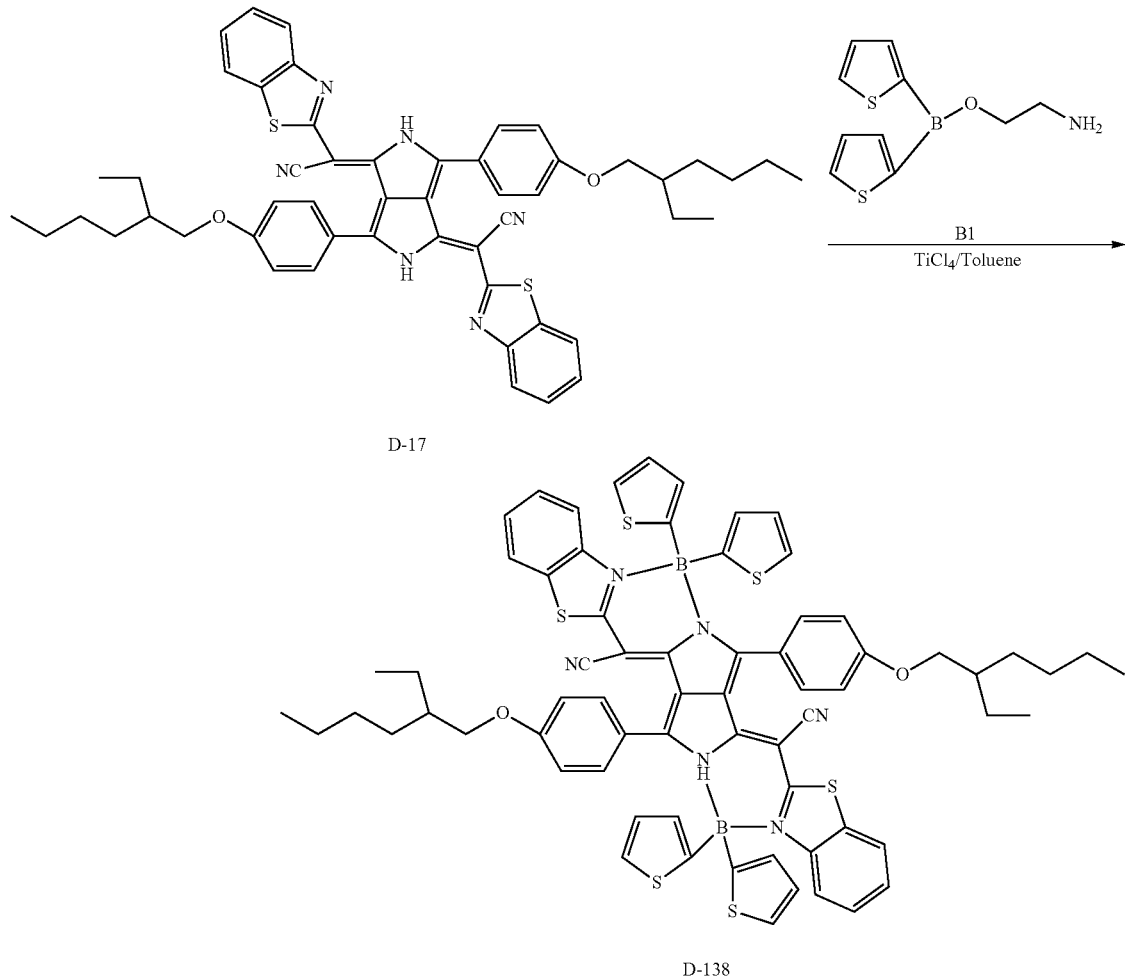

[Chemical formula 21]

D-17

D-138

Compound (B1) was synthesized in accordance with a method described in "Heterocycles", 57, (2002), p. 1319-1326.

In 20 mL of toluene, 0.86 g (1 equivalent by mol) of the exemplified compound (D-17), 0.57 g (2.4 equivalents by mol) of compound (B1) and 0.86 g of titanium tetrachloride were heated and refluxed for 1 hour. The solution was cooled to room temperature, and then thereto were added 5 mL of methyl alcohol. Thereafter, crystals were collected by filtration. The obtained crude product was purified by silica gel column chromatography (solvent: chloroform) to yield 1.0 g of the target compound (D-138) (yield: 83%).

The λmax of the exemplified compound (D-138) was 765 nm in chloroform.

The molar absorption coefficient of the exemplified compound (D-138) was $1.99 \times 10^5$ dm$^3$/mol·cm in chloroform.

$^1$H-NMR (CDCl$_3$): δ0.9-1.0 (m, 12H), 1.3-1.7 (m, 16H), 1.8 (m, 2H), 3.8 (d, 4H), 6.5 (m, 8H), 6.9 (m, 4H), 7.0 (m, 4H), 7.0-7.2 (m, 4H), 7.4 (d, 4H), 7.5 (d, 2H), 7.6 (d, 2H)

Example 12

Following exemplified compounds were prepared in the same manner as Example 11, except that the starting materials were changed. Yield, λmax, and $^1$H-NMR results for identifying the structure thereof are shown below, respectively.

Exemplified Compound (D-135)
  Yield: 92%0
  λmax: 779 nm in chloroform
  Molar absorption coefficient: $2.16 \times 10^5$ dm$^3$/mol·cm in chloroform
  $^1$H-NMR (CDCl$_3$): δ0.9-1.0 (m, 12H), 1.3-1.7 (m, 16H), 1.8 (m, 2H), 3.8 (d, 4H), 6.5 (m, 8H), 6.9 (d, 2H), 7.0-7.2 (m, 20H), 7.6 (d, 2H)

Exemplified Compound (D-136)
  Yield: 89%.
  λmax: 779 nm in chloroform

Molar absorption coefficient: $1.77 \times 10^5$ dm$^3$/mol·cm in chloroform $^1$H-NMR (CDCl$_3$): δ0.9-1.0 (m, 12H), 1.2 (s, 36H), 1.3-1.7 (m, 16H), 1.8 (m, 2H), 3.8 (d, 4H), 6.5 (m, 8H), 7.0-7.2 (m, 20H), 7.5 (d, 2H), 7.6 (d, 2H)

Exemplified Compound (D-137)

Yield: 56%.

λmax: 802 nm

Molar absorption coefficient: $1.97 \times 10^5$ dm$^3$/mol·cm in chloroform $^1$H-NMR (CDCl$_3$): δ0.7 (t, 12H), 0.9-1.0 (m, 12H), 1.1-1.2 (m, 12H), 1.3-1.4 (m, 12H), 1.3-1.7 (m, 16H), 1.8 (m, 2H), 3.8 (d, 4H), 6.9 (d, 4H), 7.3-7.4 (m, 4H), 7.5 (d, 4H), 7.7 (d, 2H), 7.9 (d, 2H)

Exemplified Compound (D-139)

Yield: 80%.

λmax: 782 nm

Molar absorption coefficient: $1.96 \times 10^5$ dm$^3$/mol·cm in chloroform $^1$H-NMR (CDCl$_3$): δ0.9-1.0 (m, 12H), 1.3-1.7 (m, 16H), 1.8 (m, 2H), 3.5 (d, 4H), 6.1 (m, 4H), 6.4 (m, 4H), 6.9-7.2 (m, 4H), 7.4-7.6 (m, 14H), 7.6-7.8 (m, 16H)

Example 13

Evaluation of Invisibility in Terms of Absorption Spectrum in Solution

Spectra of the exemplified compound (D-17) and the exemplified compound (D-9) in chloroform were each standardized to compare with each other. The results are shown in Table 1. In FIG. 1, the horizontal axis indicates a wavelength, and the vertical axis indicates an absorbance. As is apparent from FIG. 1, the exemplified compound (D-9) shows a smaller absorption in the range of from 400 nm to 500 nm than that of the exemplified compound (D-17). As a result, it is understood that the exemplified compound (D-9) is more excellent in invisibility than that of the exemplified compound (D-17).

Further, from comparison between the exemplified compound (D-1) and the exemplified compound (D-4), between the exemplified compound (D-25) and the exemplified compound (D-28), or between the exemplified compound (D-10) and the exemplified compound (D-31), it is understood that the exemplified compound (D-4), the exemplified compound (D-28) and the exemplified compound (D-31), each of which corresponds to the compound represented by the above-described formula (2), each show a smaller absorption in the range of from 400 nm to 500 nm whereby they are further excellent in invisibility.

Further, it is understood that the exemplified compound (D-6), the exemplified compound (D-11) and the exemplified compound (D-12), and other compounds represented by the above-described formula (2) according to the present invention each show a smaller absorption in the range of from 400 nm to 500 nm whereby they are further excellent in invisibility.

Example 14

Production of Fine Particles

To 10 parts by mass of the exemplified compound (D-10) and 2 parts by mass of dodecylbenzene sulfonate (DBS) as a dispersing agent, water was added to make the total amount to 500 parts by mass. Thereto were added 500 parts by mass of zirconia beads of 0.1 mmϕ, and the resultant was treated using a planet type ball mill at 300 rpm for 5 hours. An aqueous liquid dispersion containing fine particles was produced. Then the beads were separated by filtration. Nanotrac UPA particle diameter analyzer (trade name: UPA-EX150, manufactured by Nikkiso Co., Ltd.) was used to measure the particle diameter of fine particles in the aqueous liquid dispersion. The average particle diameter is 0.05 µm.

(Production of Fine Particle Dispersion Film)

To the thus-obtained aqueous liquid dispersion, a gelatin aqueous solution was added, and the resultant aqueous liquid dispersion was coated on a polyethyleneterephthalate (PET) plate provided with a gelatin undercoat layer, thereby producing a gelatin dispersion film of the exemplified compound (D-10) fine particle. An absorption spectrum of the thus-obtained gelatin film was measured. A density of the aqueous liquid dispersion was adjusted so that λmax optical density of the exemplified compound (D-10) became 1.5.

Figure 2:
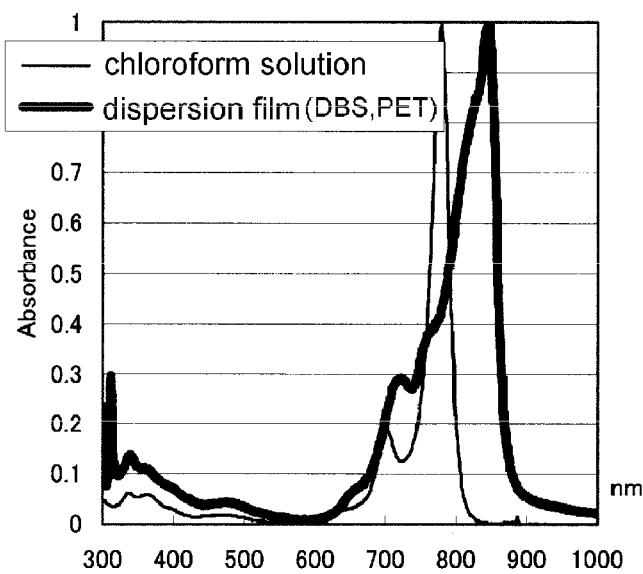
FIG. 2 is a graph showing an absorption spectrum of a gelatin dispersion film of an exemplified compound (D-10) and an absorption spectrum of the exemplified compound (D-10) in chloroform solution.
Figure 3:
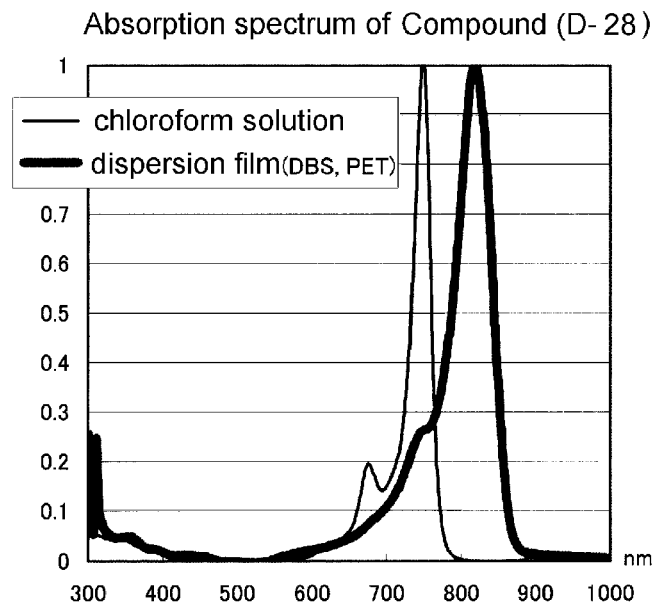
FIG. 3 is a graph showing an absorption spectrum of a gelatin dispersion film of an exemplified compound (D-28) and an absorption spectrum of the exemplified compound (D-28) in chloroform solution.

In FIG. 2, an absorption spectrum of the gelatin dispersion film of the exemplified compound (D-10) and an absorption spectrum of the exemplified compound (D-10) in chloroform solution, both of which have been standardized by λmax, are shown together. In FIG. 2, the horizontal axis indicates a wavelength, and the vertical axis indicates an absorbance. As is apparent from FIG. 2, by microparticulation, absorption wavelength of the gelatin dispersion film was made longer by 60 nm or more than the absorption wavelength in a solution, and λmax of the absorption got to 843 nm whereby excellent infrared absorbing properties were obtained. Further, absorption spectrum of the gelatin dispersion film had almost no absorption in the range of 400 nm to 700 nm. As a result, excellent invisibility was achieved.

Further, with respect to the exemplified compound (D-28), a dispersion film of the compound was produced and absorption of the dispersion film was measured in the same manner as described above. The results are shown in Table 3. As a result, it was found that the exemplified compound (D-28) has an equally excellent infrared absorbability and invisibility as the exemplified compound (D-10). Further, the same experiment was conducted, except that other compounds were used in place of the exemplified compound (D-10). As the result of the experiment, it was found that absorption spectrum of each of the dispersion films was shifted to a longer wavelength by microparticulation, and therefore it is understood that the microparticulation has an advantage in improvement of infrared-ray absorbability.

(Evaluation of Light Resistance)

As Comparative Example, a gelatin dispersion film was produced in the same manner as in the above Examples, except that an infrared absorber EXCOLOR IR-10A (trade name, manufactured by NIPPON SHOKUBAI CO., LTD.) was used.

Figure 4:
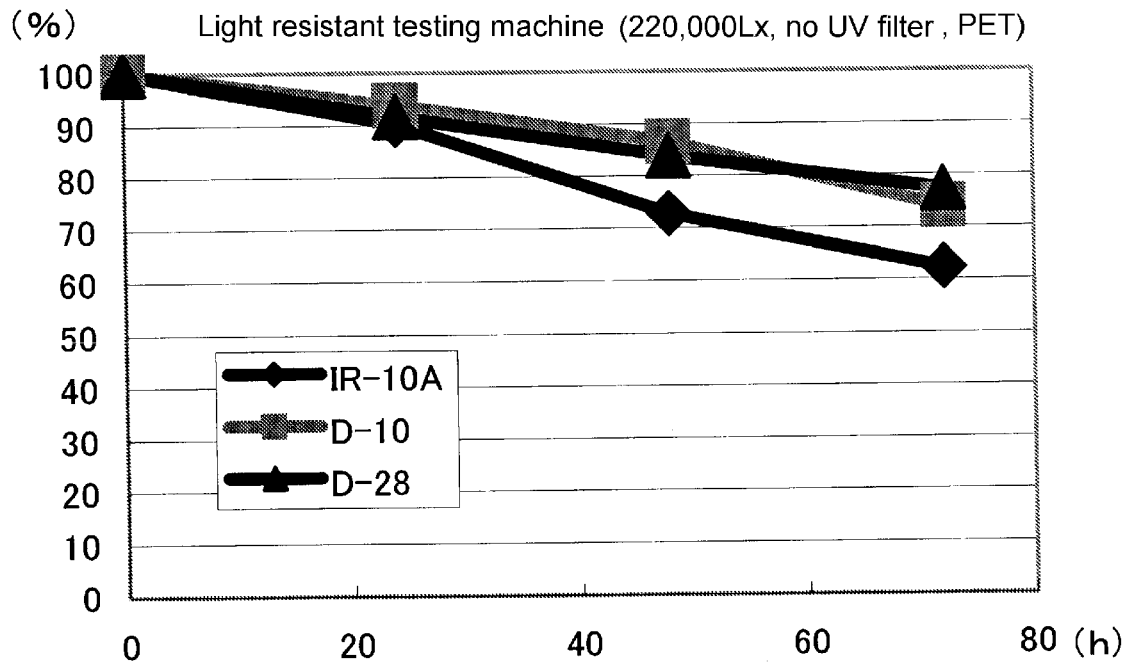
FIG. 4 is a graph showing evaluation results of light fastness of dispersion films obtained in Examples and Comparative Example.

Light resistance evaluation of each of the dispersion films obtained in the above-described Examples and Comparative Example was conducted by irradiating Xe light to the dispersion film without an UV filter using a light resistant testing machine (SUPER XENON WEATHER METER, trade name, manufactured by Suga Test Instrument Co., Ltd.; irradiance 180 W/m$^2$ at 290 nm). The results are shown in FIG. 4. In FIG. 4, the horizontal axis indicates a time (hour) and the vertical axis indicates a residual rate (%). As is apparent from the results of FIG. 4, it was found that the dispersion film using the fine particle of the exemplified compound (D-10) or (D-28) showed excellent light resistance equal to, or more than the comparative dispersion film.

Separately, an amorphous film of the exemplified compound (D-10) or (D-28) was produced. As the results of evaluating light resistance, it was found that the amorphous film was significantly inferior in light resistance to the comparative dispersion film. From these comparisons, it is understood that light resistance can be improved by microparticulation of the compound according to the present invention.

As is apparent from the above results, the fine particle of the compound of the present invention has an excellent advantage in high resistance to light in addition to both excellent infrared absorption properties and invisibility. Accordingly, the fine particle of the present invention can be applied to a marker such as a filter or an ink; industrial photothermal materials; medical materials or the like.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119(a) on Patent Application No. 2008-088959 filed in Japan on Mar. 30, 2008, which is entirely herein incorporated by reference.

The invention claimed is:

1. A dispersion, comprising:
an aqueous medium; and
fine particles which comprise a compound represented by formula (2) or (3):

[Chemical formula 2]

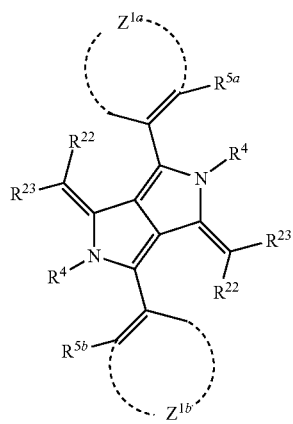

(2)

wherein, $Z^{1a}$ and $Z^{1b}$ each independently represent an atomic group that forms an aryl ring or a heteroaryl ring; $R^{5a}$ and $R^{5b}$ each independently represent an aryl group having 6 to 20 carbon atoms, a heteroaryl group having 4 to 20 carbon atoms, an alkyl group having 1 to 20 carbon atoms, an alkoxycarbonyl group having 1 to 20 carbon atoms, a carboxyl group, a carbamoyl group having 1 to 20 carbon atoms, a halogen atom, or a cyano group; $R^{5a}$ or $R^{5b}$ may be bonded to $Z^{1a}$ or $Z^{1b}$ to form a condensed ring; wherein each of $R^{5a}$ and $R^{5b}$ is in an ortho position; $R^{22}$ and $R^{23}$ each independently represent a cyano group, an acyl group having 1 to 6 carbon atoms, an alkoxycarbonyl group having 1 to 6 carbon atoms, an alkylsulfinyl or arylsufinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus; $R^4$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, and a heteroaryl group having 4 to 20 carbon atoms; and $R^4$ may be covalently bonded or coordinately bonded to $R^{23}$; and the compound may further be substituted;

[Chemical formula 3]

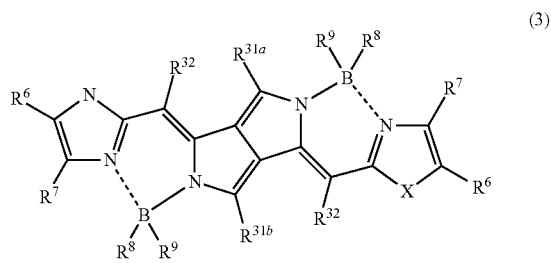

(3)

wherein, $R^{31a}$ and $R^{31b}$ each independently represent an alkyl group having 1 to 20 carbon atoms, or a heteroaryl group having 3 to 20 carbon atoms; $R^{32}$ represents a cyano group, an acyl group having 1 to 6 carbon atoms, an alkoxycarbonyl group having 1 to 6 carbon atoms, an alkylsulfinyl or arylsulfinyl group having 1 to 10 carbon atoms, or a nitrogen-containing heteroaryl group having 3 to 10 carbon atoms; $R^6$ and $R^7$ each independently represent a hydrogen atom, an alkyl group having 1 to 10 carbon atoms, an aryl group having 6 to 10 carbon atoms, or a heteroaryl group having 4 to 10 carbon atoms; $R^6$ may be bonded to $R^7$ to form a ring, and the formed ring is an alicyclic ring having 5 to 10 carbon atoms, an aryl ring having 6 to 10 carbon atoms, or a heteroaryl ring having 3 to 10 carbon atoms; $R^8$ and $R^9$ each independently represent an alkyl group having 1 to 10 carbon atoms, an alkoxy group having 1 to 10 carbon atoms, an aryl group having 6 to 20 carbon atoms, or a heteroaryl group having 3 to 10 carbon atoms; and X represents an oxygen atom, a sulfur atom, —NR—, or —CRR'—; in which R and R' each independently represent a hydrogen atom, an alkyl group having 1 to 10 carbon atoms, or an aryl group having 6 to 10 carbon atoms wherein a particle diameter of the fine particles is 1 nm or more and 1000 nm or less.

2. The dispersion according to claim 1, wherein $R^{23}$ in formula (2) is a heterocyclic group.

3. The dispersion according to claim 1, wherein the particle is an infrared absorptive particle which absorbs infrared rays in a wavelength range of 700 nm or more and 1000 nm or less.

4. A coated material which comprises the dispersion according to claim 1.

5. The dispersion according to claim 1, which further comprises a surfactant.

6. An infrared absorbing film which is obtained by coating the dispersion according to claim 1.

7. The dispersion according to claim 1, wherein the fine particles comprise a compound represented by formula (2).

8. An infrared absorptive compound represented by formula (2):

[Chemical formula 2]

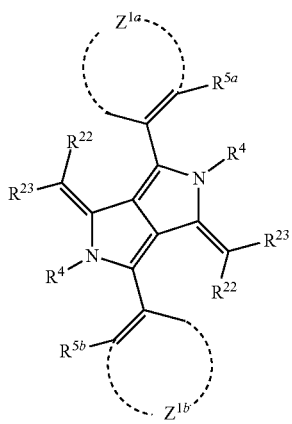

(2)

wherein, $Z^{1a}$ and $Z^{1b}$ each independently represent an atomic group that forms an aryl ring or a heteroaryl ring; $R^{5a}$ and $R^{5b}$ each independently represent an aryl group having 6 to 20 carbon atoms, a heteroaryl group having 4 to 20 carbon atoms, an alkyl group having 1 to 20 carbon atoms, an alkoxycarbonyl group having 1 to 20 carbon atoms, a carboxyl group, a carbamoyl group having 1 to 20 carbon atoms, a halogen atom, or a cyano group; $R^{5a}$ or $R^{5b}$ may be bonded to $Z^{1a}$ or $Z^{1b}$ to form a condensed ring; wherein each of $R^{5a}$ and $R^{5b}$ is in an ortho position; $R^{22}$ and $R^{23}$ each independently represent a cyano group, an acyl group having 1 to 6 carbon atoms, an alkoxycarbonyl group having 1 to 6 carbon atoms, an alkylsulfinyl or arylsufinyl group having 1 to 10 carbon atoms, or a nitrogen-containing heteroaryl group having 3 to 20 carbon atoms, or $R^{22}$ and $R^{23}$ are bonded to each other to form a cyclic acidic nucleus; $R^4$ represents a hydrogen atom, an alkyl group having 1 to 20 carbon atoms, an aryl group having 6 to 20 carbon atoms, a heteroaryl group having 4 to 20 carbon atoms, a metal atom, or a substituted boron having at least one substituent selected from a halogen atom, an alkyl group having 1 to 10 carbon atoms, an aryl group having 6 to 20 carbon atoms, or a heteroaryl group having 4 to 20 carbon atoms; and $R^4$ may be covalently bonded or coordinately bonded to $R^{23}$; and the compound may further be substituted.

\* \* \* \* \*